United States Patent
Saly et al.

(10) Patent No.: US 10,022,328 B2
(45) Date of Patent: Jul. 17, 2018

(54) DIALKYL SULFOSUCCINATE COMPOSITIONS, METHOD OF MAKING, AND METHOD OF USE

(71) Applicant: CYTEC INDUSTRIES INC., Princeton, NJ (US)

(72) Inventors: Eric Saly, Dordrecht (NL); Maureen Mackay, Cheshire (GB); Matthias Rischer, Frankfurt (DE); Wolfgang Mohr, Freiburg i. Br. (DE); Lena Kurz, Lörrach (DE)

(73) Assignee: Cytec Industries Inc., Princeton, NJ (US)

( * ) Notice: Subject to any disclaimer, the term of this patent is extended or adjusted under 35 U.S.C. 154(b) by 0 days.

(21) Appl. No.: 15/046,648

(22) Filed: Feb. 18, 2016

(65) Prior Publication Data
US 2016/0317445 A1 Nov. 3, 2016

Related U.S. Application Data

(60) Provisional application No. 62/287,198, filed on Jan. 26, 2016, provisional application No. 62/118,786, filed on Feb. 20, 2015.

(51) Int. Cl.
*A61K 9/16* (2006.01)
*A61K 9/14* (2006.01)
(Continued)

(52) U.S. Cl.
CPC ............ *A61K 9/1617* (2013.01); *A61K 9/145* (2013.01); *A61K 9/146* (2013.01); *A61K 9/1623* (2013.01);
(Continued)

(58) Field of Classification Search
CPC .. A61K 9/1635; A61K 9/1647; A61K 9/1694; A61K 9/1652
See application file for complete search history.

(56) References Cited

U.S. PATENT DOCUMENTS

| | | | |
|---|---|---|---|
| 2,028,091 A | 1/1936 | Jaeger | |
| 2,441,341 A * | 5/1948 | Vitalis | C11D 1/123 |
| | | | 252/363.5 |

(Continued)

FOREIGN PATENT DOCUMENTS

| | | | |
|---|---|---|---|
| WO | 0224163 A1 | 3/2002 | |
| WO | 200224163 A1 * | 3/2002 | |

(Continued)

OTHER PUBLICATIONS

Esumi et al.; "Interaction between Aerosol OT andPoly(vinylpyrrolidone) on Alumina"; Langmuir, vol. 10; 1994; 3250-3254.

(Continued)

*Primary Examiner* — Carlos A Azpuru
(74) *Attorney, Agent, or Firm* — Dennis J. Jakiela; Charles E. Bell

(57) ABSTRACT

A particulate solid composition comprises a blend of dialkyl sulfosuccinate and a water-soluble polymer. The water-soluble polymer can be a cellulose ether, a polysaccharide, a polyvinyl alcohol homopolymer or copolymer, a polyvinyl pyrrolidone homopolymer or copolymer, a polyvinyl caprolactam polymer or copolymer, a poly(meth)acrylate, a poly (alkylene oxide) graft copolymer, or a combination thereof. The particulate solid composition is free flowing, water-soluble, and dissolves rapidly in water. It can be made by drying a solution of dialkyl sulfosuccinate and a water-soluble polymer. The particulate solid composition can be mixed with organic substances having low water solubility, for example a generic, a biologic, a biosimilar, an excipient, (Continued)

a nutraceutical, a medical diagnostic agent, an agricultural chemical, or a combination thereof, to form water-soluble compositions.

34 Claims, 14 Drawing Sheets

(51) Int. Cl.
*A61K 31/192* (2006.01)
*A61K 31/235* (2006.01)
*A61K 31/64* (2006.01)
*A61K 38/05* (2006.01)

(52) U.S. Cl.
CPC .......... *A61K 9/1635* (2013.01); *A61K 9/1641* (2013.01); *A61K 9/1647* (2013.01); *A61K 9/1652* (2013.01); *A61K 31/192* (2013.01); *A61K 31/235* (2013.01); *A61K 31/64* (2013.01); *A61K 38/05* (2013.01)

(56) References Cited

U.S. PATENT DOCUMENTS

| | | |
|---|---|---|
| 5,145,684 A | 9/1992 | Liversidge et al. |
| 5,426,163 A | 6/1995 | Buehler et al. |
| 5,834,565 A | 11/1998 | Tracy et al. |
| 6,375,986 B1 | 4/2002 | Ryde et al. |
| 2002/0110597 A1 | 8/2002 | Ryde et al. |
| 2010/0086592 A1 | 4/2010 | Singh et al. |

FOREIGN PATENT DOCUMENTS

| | | |
|---|---|---|
| WO | 02094215 A2 | 11/2002 |
| WO | 2007110875 A1 * | 10/2007 |
| WO | 2010006697 A2 * | 1/2010 |

OTHER PUBLICATIONS

Evonik Industries AG; "EUDRAGIT® E 100, EUDRAGIT® E PO and EUDRAGIT® E 12,5"; EUDRAGIT® E 100, EUDRAGIT® E PO, EUDRAGIT® E 12,5; May 2014, 6 pages.
Evonik Industries AG; "EUDRAGIT® E PO"; EUDRAGIT, Quickstart; Dec. 2011, 2 pages.
Ghebremeskel et al.; "Use of surfactants as plasticizers in preparing solid dispersions of poorly soluble API . . . "; International Journal of Pharmaceutics, vol. 328, 2007, pp. 119-129.
International Search Report for International Application No. PCT/US2016/018428, International Filing Date Feb. 18, 2016, dated May 23, 2016, 6 pages.
Kadajji et al.; "Water Soluble Polymers for Pharmaceutical Applications"; Polymers; vol. 3, 2011, pp. 1972-2009.
Nikam et al.; "EUDRAGIT a Versatile Polymer: A Review"; Pharmacologyonline; vol. 1; 2011, pp. 152-164.
Volker Buhler; "Kollidon® Polyvinylpyrrolidone excipients for the pharmaceutical industry", 9th revised edition; Mar. 2008, 331 pages.
Written Opinion for International Application No. PCT/US2016/018428, International Filing Date Feb. 18, 2016, dated May 23, 2016, 6 pages.

* cited by examiner

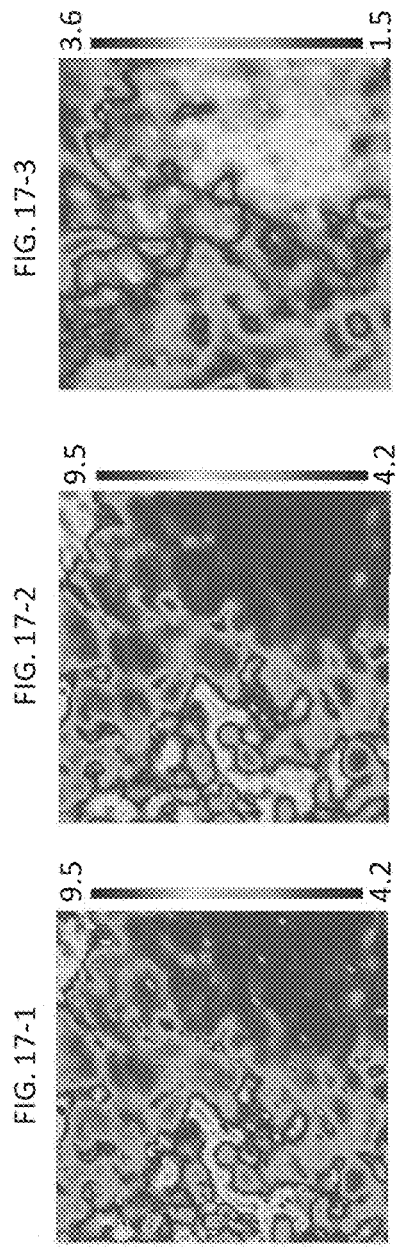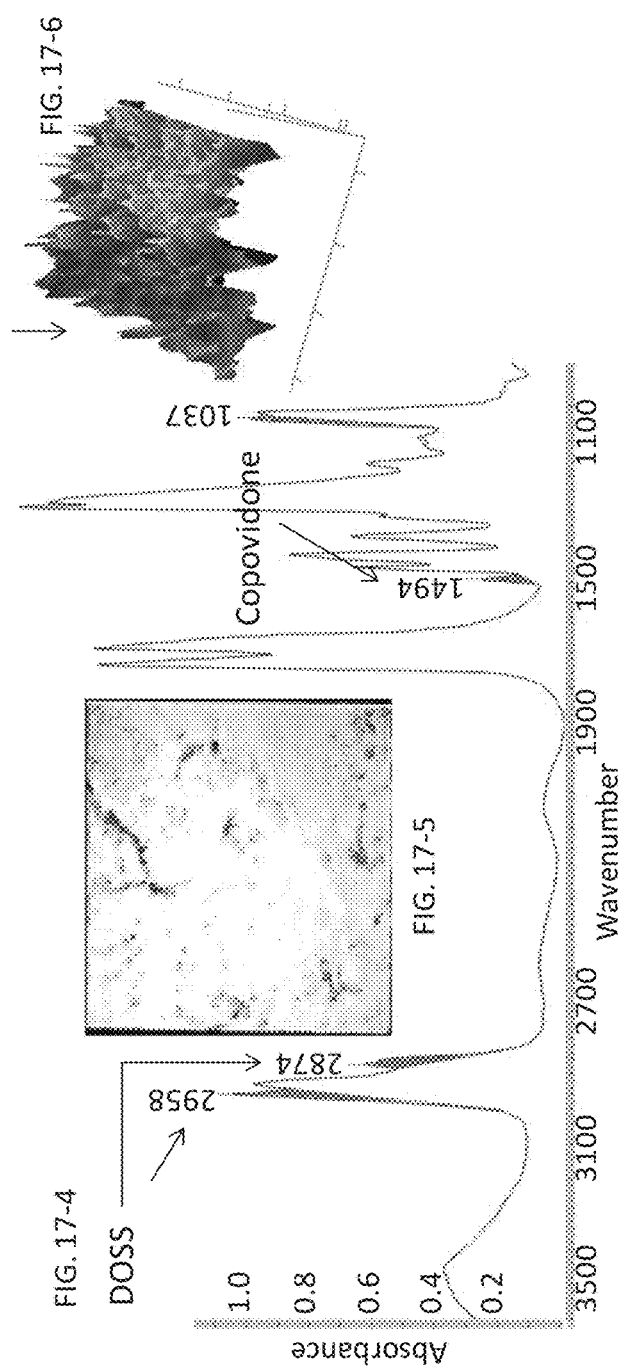
FIG. 17

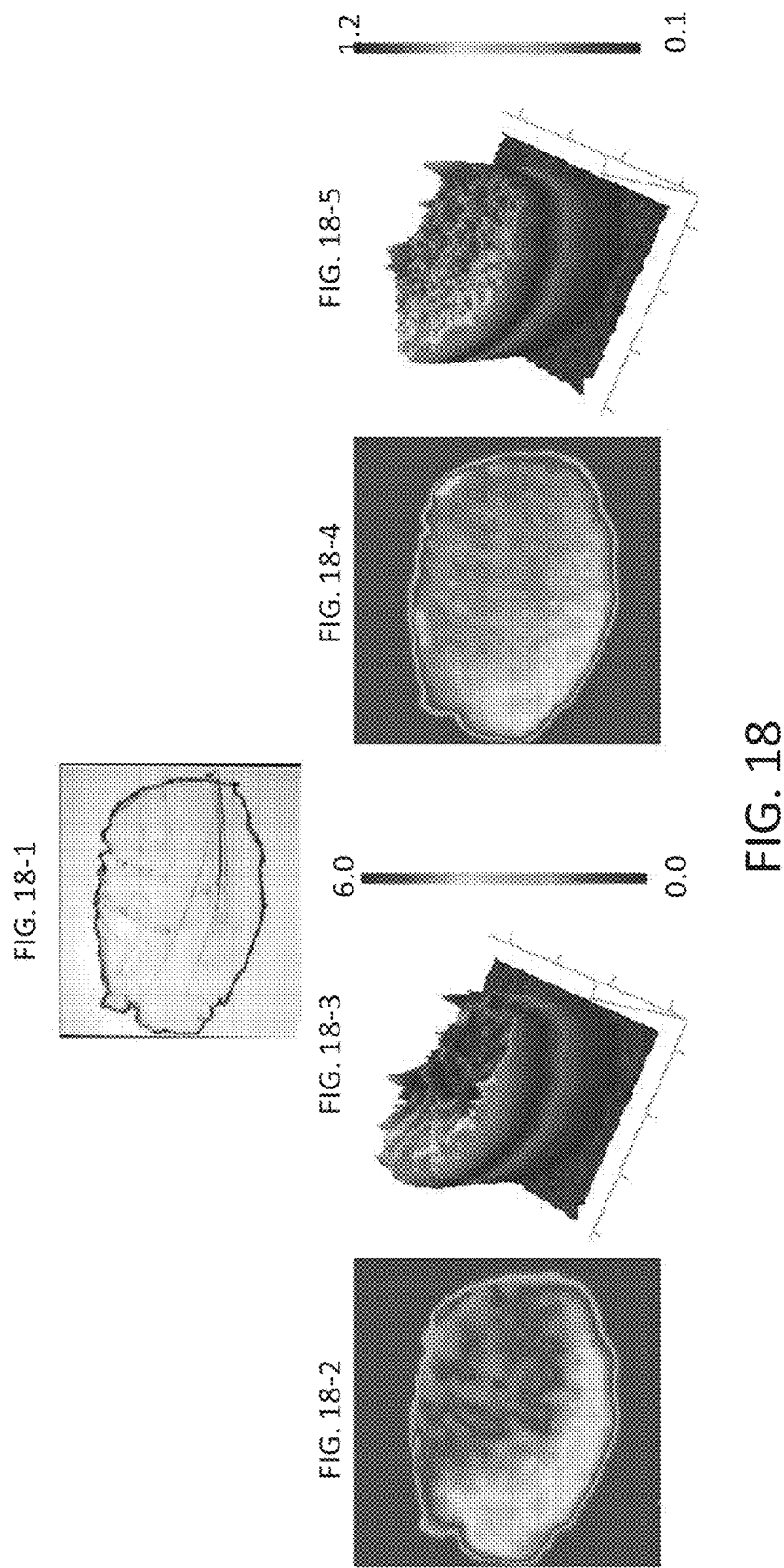

DIALKYL SULFOSUCCINATE COMPOSITIONS, METHOD OF MAKING, AND METHOD OF USE

CROSS REFERENCE TO RELATED APPLICATIONS

This non-provisional application claims priority to U.S. Provisional Application Nos. 62/118,786, filed Feb. 20, 2015, and 62/287,198, filed Jan. 26, 2016, both of which are incorporated herein by reference in their entirety.

BACKGROUND OF THE INVENTION

Dialkyl sulfosuccinates are a class of surfactants used as emulsifiers, dispersants, wetting agents, and adjuvants. An example of a dialkyl sulfosuccinate is sodium dioctyl sulfosuccinate (DOSS). DOSS is a waxy, sticky, granular solid, which is difficult to handle. It tends to form lumps upon storage, and is slow to dissolve in solvents. Therefore it is often supplied in solution form, dissolved in organic solvent, water, or organic solvent-water combinations, for example ethanol-water and propylene glycol-water. DOSS can also be mixed with a solid diluent, for example sodium benzoate (SB), to produce a mixture (DOSS-SB) with reduced stickiness and improved water dissolution rate. However, the water solubility and dissolution rates of DOSS-SB mixtures are still low. Sodium benzoate is used as a food preservative and is pharmacologically active. However, its use as an excipient for other active pharmaceutical ingredients can be undesirable, because it is not biologically inert, and because of the risk of formation of benzene from sodium benzoate in the presence of ascorbic acid.

A dialkyl sulfosuccinate composition containing a solid diluent that is free of sodium benzoate, and yet is not waxy or sticky, has good flowability and water solubility, and dissolves rapidly in water, is desirable. Also, the surface and wetting activity of the dialkyl sulfosuccinate, as indicated by critical micelle concentration and contact angle of aqueous solutions of the dialkyl sulfosuccinate with various substrates, should not be adversely affected by the solid diluent.

BRIEF DESCRIPTION OF THE INVENTION

A particulate solid composition comprises a blend of dialkyl sulfosuccinate and a water-soluble polymer.

A method of making a particulate solid composition, comprises: mixing a dialkyl sulfosuccinate and a water-soluble polymer in a solvent to form a solution, and spray drying the solution to form the particulate solid composition, wherein: the particulate solid composition comprises primary particles having a diameter range from 1 to 50 micrometers, as measured by scanning electron microscopy; and comprises, based on the total weight of the composition, 0 to less than 5 weight percent each of active pharmaceutical ingredients, generics, biologics, biosimilars, excipients, nutraceuticals, diagnostic agents, and agricultural chemicals.

A method of making a particulate solid composition, comprises: mixing a dialkyl sulfosuccinate and a water-soluble polymer in a solvent to form a solution; contacting the solution with a heated surface; and removing the solvent to form the particulate solid composition, wherein the particulate solid composition comprises flakes, and comprises, based on the total weight of the composition, 0 to less than 5 weight percent each of active pharmaceutical ingredients, generics, biologics, biosimilars, excipients, nutraceuticals, diagnostic agents, and agricultural chemicals.

A method of making a water-soluble composition, comprises mixing a particulate solid composition and an organic substance having low water solubility, in amounts effective to form the water-soluble composition; wherein: the particulate solid composition comprises a blend of dialkyl sulfosuccinate, a water-soluble polymer, and 0 to less than 5 weight percent each of active pharmaceutical ingredients, generics, biologics, biosimilars, excipients, nutraceuticals, diagnostic agents, and agricultural chemicals, based on the total weight of the water-soluble composition; the particulate solid composition has a distilled water solubility of 1 to 20 weight percent at 23° C., with no haze; and the organic substance has a water solubility of less than 1 weight percent at 23° C.

BRIEF DESCRIPTION OF THE DRAWINGS

Referring now to the drawings:

FIGS. 14-1, 14-2, and 14-3 are two-dimensional visible, DOSS-specific FTIR, and HPMC-specific FTIR images of a first sample, and FIGS. 14-4, 14-5, and 14-6 are two-dimensional visible, DOSS-specific FTIR, and HPMC-specific FTIR images of a second sample. FIG. 14-7 and FIG. 14-8 are three-dimensional HPMC-specific and DOSS-specific FTIR images for the first sample. FIG. 14-9 depicts overlaid one-dimensional FTIR spectra of DOSS and HPMC indicating the analytical wavelengths of 1735 and 1064 $cm^{-1}$, respectively, which were used to generate the two- and three-dimensional images of FIGS. 14-2, 14-3, and 14-5 to 14-8.

FIG. 17 depicts a visible micrograph (FIG. 17-5) and FTIR vibrational images, measured in transmission mode, of compressed particle aggregates of DOSS-copovidone with 350×350 micrometer fields of view, including DOSS-specific images (FIGS. 17-1 and 17-2) and copovidone-specific images (FIGS. 17-3 and 17-6). The DOSS-specific image of FIG. 17-1 was generated at an analytical wavelength of 2958 $cm^{-1}$; the DOSS-specific image of FIG. 17-2 was generated at 2874 $cm^{-1}$; and the copovidone-specific images of FIGS. 17-3 and 17-6 were generated at 1494 $cm^{-1}$. FIG. 17-6 is a three-dimensional image of copovidone distribution. FIG. 17-4 depicts overlaid one-dimensional FTIR spectra of DOSS and copovidone, indicating the analytical wavelengths of 2874 and 2958 $cm^{-1}$ for DOSS, which were used to generate the two-dimensional images of FIGS. 17-1 and 17-2, respectively; and the analytical wavelength of 1094 $cm^{-1}$, which was used to generate the two-dimensional image of FIG. 17-3 and the three-dimensional image of FIG. 17-6.

FIG. 18 depicts a visible micrograph (FIG. 18-1) and FTIR vibrational images, measured in transmission mode, of a compressed sample of DOSS-copovidone with a 350×350 micrometer field of view, including DOSS-specific images (FIGS. 18-2 and 18-3) and copovidone-specific images (FIGS. 18-4 and 18-5). The DOSS-specific image of FIG. 18-2 was generated at an analytical wavelength of 2874 $cm^{-1}$; and the copovidone-specific image of FIG. 18-4 was generated at 1494 $cm^{-1}$. FIGS. 18-3 and 18-5 are three-dimensional images of the DOSS and copovidone distributions, respectively.

DETAILED DESCRIPTION OF THE INVENTION

Figure 1:
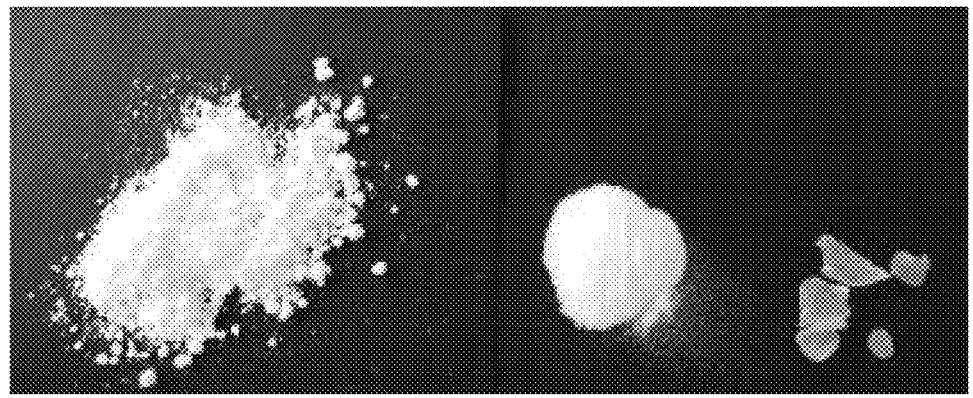
FIG. 1 depicts photographs of DOSS (right), HPMC (center), and the DOS-HPMC of Example 3 (left).

Dialkyl sulfosuccinates, for example, sodium dioctyl sulfosuccinate (DOSS) are generally supplied mixed with liquid or solid diluents, for example sodium benzoate (SB), to improve handling. Typically pure DOSS is in the form of sticky, waxy flakes. The present inventors have made dialkyl sulfosuccinate powder blends in which the diluent is a water-soluble polymer. When spray-dried or vacuum drum dried, the present dialkyl sulfosuccinate powder blends are microscopic, spherical or flake particles with an amorphous matrix in which the crystalline DOSS is dispersed. Advantageously, the dialkyl sulfosuccinate blends are free-flowing, water-soluble solids which dissolve rapidly in water. Moreover, the surface and wetting activity of the dialkyl sulfosuccinate, as indicated by critical micelle concentration and contact angle of aqueous solutions of the dialkyl sulfosuccinate with various substrates, is not adversely affected by the water-soluble polymer.

The inventors have found a particulate solid composition comprising a blend of dialkyl sulfosuccinate and a water-soluble polymer. The dialkyl sulfosuccinate has the chemical structure:

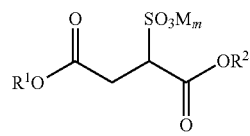

wherein $R^1$ and $R^2$ are each independently a linear or branched, $C_{4-18}$ alkyl, specifically $C_{4-12}$ alkyl, more specifically $C_{4-8}$ alkyl, $C_{5-18}$ cycloalkyl, $C_{7-18}$ arylalkyl, or $C_{6-18}$ aryl, unsubstituted or substituted by hydroxyl or $C_{1-18}$ alkoxy, more specifically $C_{1-4}$ alkoxy. The cation "M" can be an ammonium or quaternary ammonium ion. In some embodiments, M is an alkali metal, an alkaline earth metal, an ammonium ion, or a combination thereof, and m is 0.5 when M is an alkaline earth metal, and m is 1 when M is an alkali metal or ammonium ion. M can be for example, lithium sodium, potassium, or calcium. In some embodiments, M is sodium. In some embodiments, $R^1$ and $R^2$ are each independently a linear or branched $C_{4-12}$ alkyl, specifically $C_{4-8}$ alkyl. For example, $R^1$ and $R^2$ can each independently be amyl, hexyl, octyl, nonyl, dodecyl, or stearyl. Since these alkyl groups can be branched, octyl can be 2-ethylhexyl. Thus in some embodiments, $R^1$ and $R^2$ are both 2-ethylhexyl, M is sodium, and m is 1. This specific dialkyl sulfosuccinate is known as "sodium dioctyl sulfosuccinate", and is referred to herein as "DOSS". DOSS is available from Solvay S.A. as Docusate Sodium.

The particulate solid composition comprises a water-soluble polymer. The water soluble polymer can be natural, semi-synthetic, synthetic, or a combination thereof. Natural water soluble polymers include albumin, and polysaccharides such as xanthan gum, pectin, dextran, carrageenan, guar gum, galactomannan, alginate, xanthan gum, starch, hyaluronic acid, chitin, and chitosan. Semi-synthetic water soluble polymers include starch derivatives (blends or chemically modified), for example a cyclodextrin. Semi-synthetic water soluble polymers can also include chemically modified cellulose, for example hydroxypropylmethyl cellulose (HPMC), hydroxypropyl cellulose (HPC), hydroxyethyl cellulose (HEC), and sodium carboxy methyl cellulose (Na-CMC).

Synthetic water-soluble polymers include addition polymers of ethylenically unsaturated monomers, and can be homopolymers or copolymers, for example, a random copolymer, an alternating copolymer, a periodic copolymer, a block copolymer, a graft copolymer, or a branched copolymer. The water-soluble polymer architecture can be, for example, star, comb, brush, or dendritic. Examples of synthetic water-soluble addition polymers include polyvinyl alcohol homopolymers and copolymers, poly(vinyl pyrrolidone) homopolymers and copolymers, poly(vinyl caprolactam) homopolymers and copolymers, poly (meth)acrylic acid homopolymers and copolymers, poly(meth)acrylamide homopolymers and copolymers, polyoxazoline homopolymers and copolymers, vinyl ether homopolymers and copolymers, and polymaleic anhydride homopolymers and copolymers. Other examples of synthetic water-soluble polymers include poly(alkylene oxide) homopolymers and copolymers, for example poloxamers, polyphosphates, and polyphosphazenes.

In particular, the water-soluble polymer can comprise a cellulose ether, a polysaccharide, a polyvinyl alcohol homopolymer or copolymer, a poly(vinyl pyrrolidone) homopolymer or copolymer, a polyvinyl caprolactam polymer or copolymer, a poly(meth)acrylate, a poly(alkylene oxide), a poly(alkylene oxide) block or graft copolymer, or a combination thereof. In some embodiments, the water-soluble polymer comprises hydroxypropyl cellulose, hydroxypropylmethyl cellulose, poly(vinyl pyrrolidone), poly(vinyl pyrrolidone-co-vinyl acetate), polyvinyl alcohol, poly(vinyl acetate-co-vinyl alcohol), poly(ethylene oxide-co-vinyl acetate-co-vinyl caprolactam), or a combination thereof.

In some embodiments, the water-soluble polymer is hydroxypropylmethyl cellulose (HPMC). An example of HPMC is PHARMACOAT™ 603, having a methoxy content of 28.0 to 30.0 weight percent, a hydroxypropoxy content of 7.0 to 12.0 wt %, and a viscosity of 2.4 to 3.6 mPa·s, available from Shin-Etsu Chemical.

The water-solubility of poly(vinyl pyrrolidone-co-vinyl acetate) depends on the vinyl pyrrolidone/vinyl acetate comonomer ratio. Thus, the water-soluble polymer can comprise poly(vinyl pyrrolidone-co-vinyl acetate) having copolymerized vinyl pyrrolidone and vinyl acetate repeat units in a 50:50 to 99:1 weight ratio. In some embodiments, the water-soluble polymer comprises poly(vinyl pyrrolidone-co-vinyl acetate) having copolymerized vinyl pyrrolidone and vinyl acetate repeat units in a 6:4 weight ratio, which is commercially available from BASF as KOLLIDON™ VA 64.

In some embodiments, the polymers are defined as water soluble if the solubility is greater than or equal to 0.1 g/L when dissolved in pH 1.2 HCl buffer for 40 minutes at 37° C. Within this range the solubility can be greater than 1 g/L, or greater than 10 g/L, and less than 1,000 g/L, less than 900 g/L, less than 800 g/L, less than 700 g/L, less than 600 g/L, or less than 500 g/L. In some embodiments the polymers are defined as water soluble if the solubility is greater than 0.1 g/L when dissolved in pH 6.8 phosphate buffer for 40 minutes at 37° C. Within this range the solubility can be greater than 1 g/L, or greater than 10 g/L, and less than 1,000 g/L, less than 900 g/L, less than 800 g/L, less than 700 g/L, less than 600 g/L, or less than 500 g/L. The water-soluble polymer can be miscible with pH 1.2 HCl and pH 6.8 phosphate buffers in all proportions. However, as the water-soluble polymer concentration is increased, the resulting solution can become so viscous at 37° C. that the solution can no longer be stirred. As a practical matter, the upper limit in solubility can be determined by this phenomenon. An example of a water-soluble polymer that is soluble in pH 1.2 HCl buffer is poly(butyl methacrylate-co-2-dimethylaminoethyl methacrylate-co-methyl methacrylate), having copolymerized 2-dimethylaminoethyl methacrylate, butyl methacrylate, and methyl methacrylate repeat units in a 2:1:1 weight ratio, respectively, which is commercially available as EUDRAGIT™ E PO.

The particle morphology of the particulate solid composition can depend on the method of making the composition. For example, spherical particles can be obtained by spray drying. Thus in some embodiments, the particulate solid composition is composed of primary particles that are microscopic and spherical. The particle diameter range can be from 1 to 50 micrometers, as determined by scanning electron microscopy (SEM). Within this range, the particle diameter range can be 1 to 40 micrometers, specifically 1 to 30 micrometers. In some embodiments, the particle diameter range is 1 to 25 micrometers, specifically 2 to 25 micrometers, and more specifically 2 to 15 micrometers.

Figure 3A:
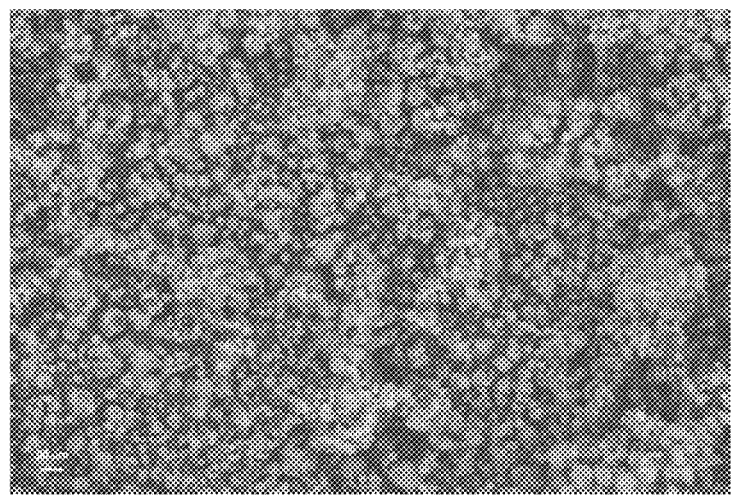
FIG. 3a, FIG. 3b, and FIG. 3c depict SEM photographs of the DOSS-HPMC of Example 3 at magnifications of 500×, 3,000× and 5,000×, respectively.
Figure 3B:
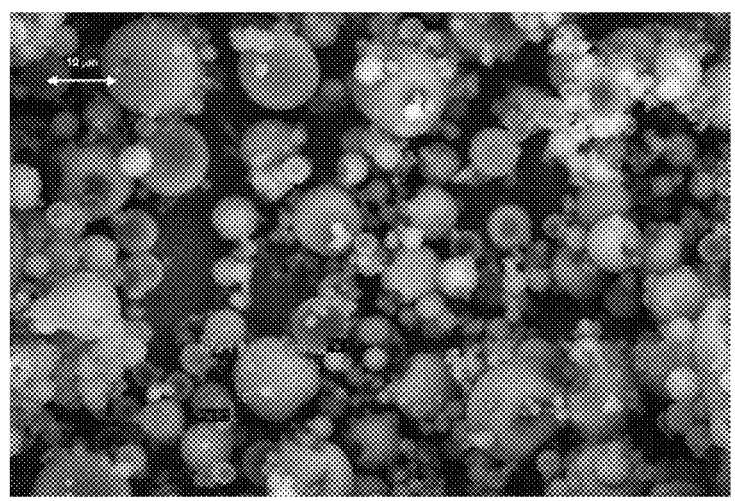
Figure 3C:
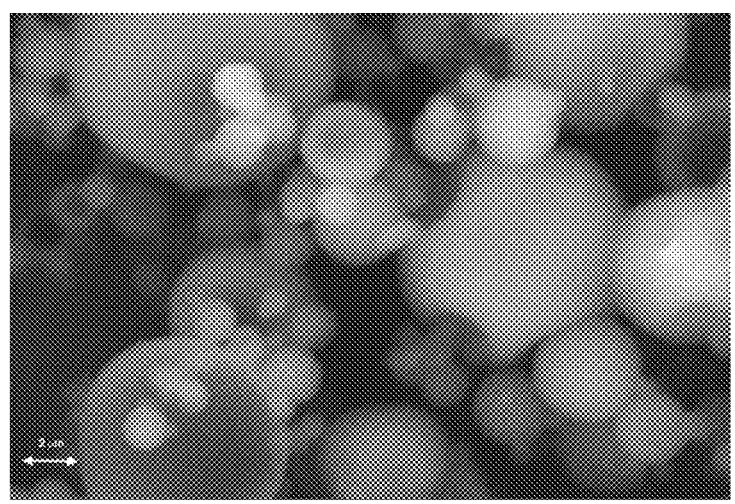
Figure 4A:
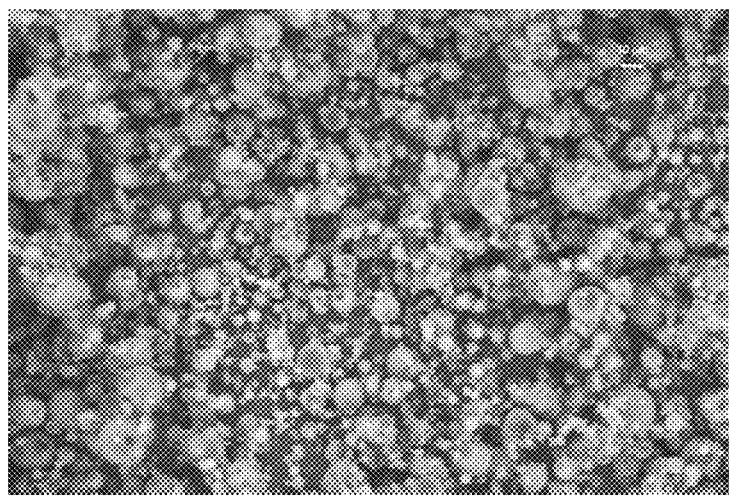
FIG. 4a, FIG. 4b, and FIG. 4c depict SEM photographs of the DOSS-copovidone of Example 3 at magnifications of 1,000×, 2,000× and 5,000×, respectively.
Figure 4B:
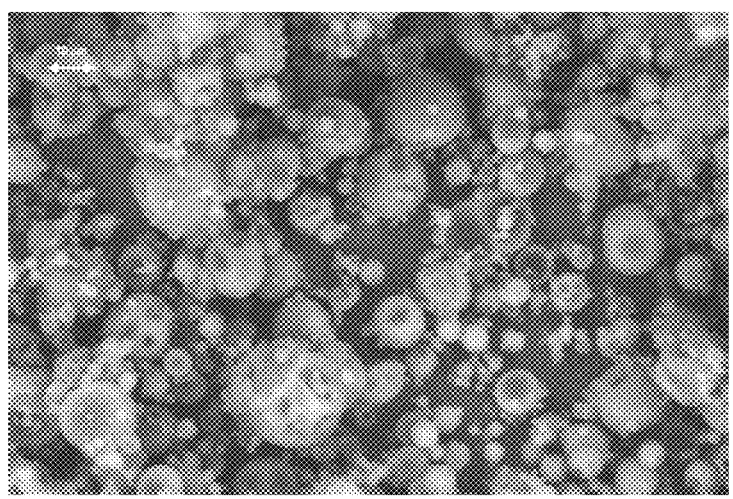
Figure 4C:
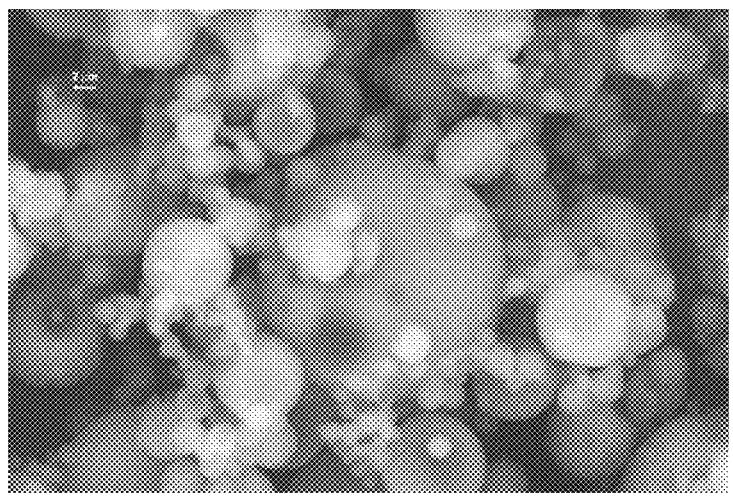
Figure 5A:
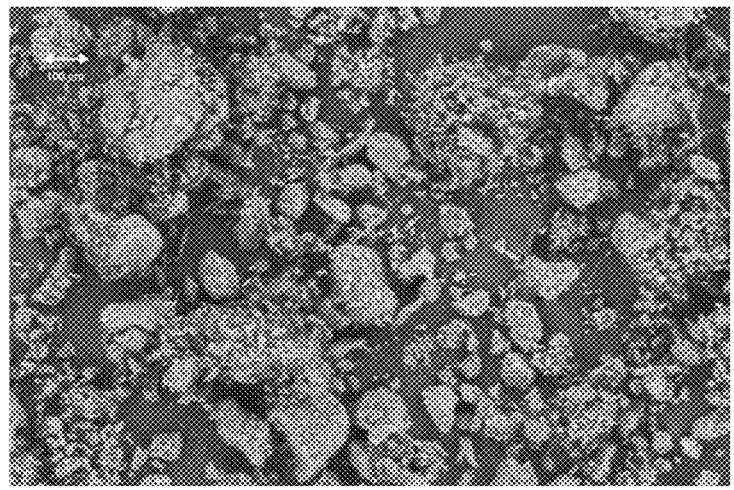
FIG. 5a, FIG. 5b, and FIG. 5c depict SEM photographs of the DOSS-SB of Comparative Example 1 at magnifications of 200×, 500× and 1,000×, respectively.
Figure 5B:
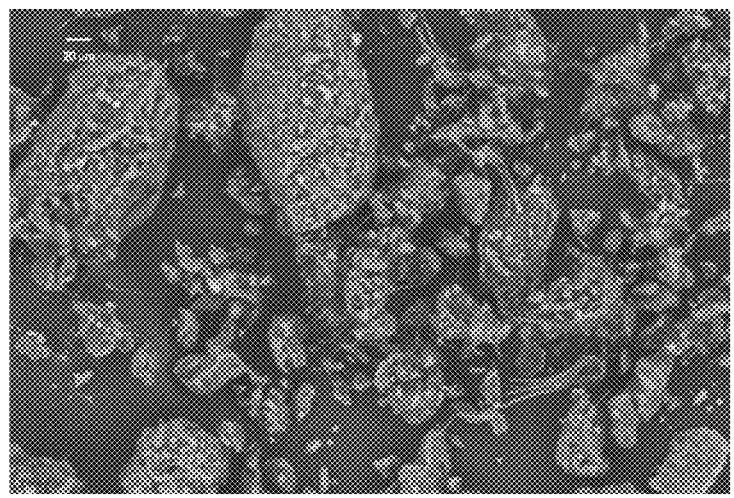
Figure 5C:
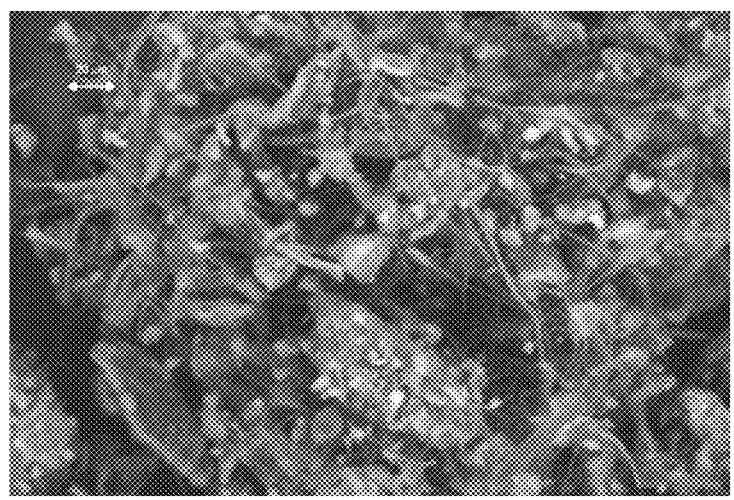

FIG. 3a, FIG. 3b, and FIG. 3c depict SEM photographs of the DOSS-HPMC of Example 3 at magnifications of 500×, 3,000× and 5,000×, respectively. FIG. 4a, FIG. 4b, and FIG. 4c depict SEM photographs of the DOSS-copovidone of Example 3 at magnifications of 1,000×, 2,000× and 5,000×, respectively. FIG. 5a, FIG. 5b, and FIG. 5c depict SEM photographs of the DOSS-SB of Comparative Example 1 at magnifications of 200×, 500× and 1,000×, respectively. As can be seen from the SEM photographs, the DOSS-HPMC and DOSS-copovidone particles are spherical, while the DOSS-SB particles are irregularly-shaped. HPMC particles were macroscopic and irregularly-shaped. Advantageously, the DOSS-HPMC and DOSS-copovidone blends have a particle diameter range of 2 to 15 micrometers, while the DOSS-SB blend has a particle diameter range of about 100 micrometers and above, as determined by SEM.

Under some conditions, the primary particles, once formed, can combine to form agglomerates. Thus in some embodiments, the particulate solid composition further comprises aggregates of the primary particles, wherein the aggregates have a diameter range from 0.1 to 2 millimeters, as determined by optical microscopy. Within this range, the particle diameter of the aggregates can be 0.1 to 1 millimeters.

As mentioned above, the particle morphology of the particulate solid composition can depend on the method of making the composition. For example, flat particles can be obtained by drum drying. Thus in some embodiments, the particulate solid composition comprises flakes. The flakes can be irregular in shape, and can have a thickness of 1 to 100 micrometers, as determined by scanning electron microscopy. Within this range, the flakes can have a thickness of 1 to 50 micrometers, 1 to 20 micrometers, or 1 to 10 micrometers. In some embodiments, the flakes have a thickness of 1 to 10 micrometers. The flakes can be obtained, for example by vacuum drum drying.

The particulate solid composition can be amorphous. Amorphous particles lack the long-range inter-molecular order of crystalline solids, and lack sharp crystalline X-ray diffraction (XRD) peaks. This is in contrast to physical mixtures of dioctyl sulfosuccinate and sodium benzoate, which can be crystalline.

In some embodiments, the particulate solid composition comprises a blend of crystalline dialkyl sulfosuccinate and amorphous or semi-crystalline water-soluble polymer. Powder X-ray diffraction (PXRD) was used to assess the crystallinity of the compositions. The diffraction patterns of, for example DOSS-copovidone and DOSS-HPMC, both indicate the presence of both crystalline DOSS and amorphous or semi-crystalline copovidone or HPMC in the compositions.

In some embodiments, the amorphous particulate solid composition comprises 10 to 90 weight percent of the dialkyl sulfosuccinate and 10 to 90 weight percent of the water-soluble polymer, based on the total weight of the dialkyl sulfosuccinate and water-soluble polymer. Within this range, the particulate solid composition can comprise greater than or equal to 20 or 30 weight percent and less than or equal to 80 or 70 weight percent of dialkyl sulfosuccinate, and greater than or equal to 20 or 30 weight percent and less than or equal to 80 or 70 weight percent of water-soluble polymer. For example, the particulate solid composition can comprise 10 to 70 weight percent, 20 to 50 weight percent, or 20 to 40 weight percent of the dialkyl sulfosuccinate, and 30 to 90 weight percent, 50 to 80 weight percent, or 60 to 80 weight percent of the water-soluble polymer, based on the total weight of the dialkyl sulfosuccinate and water-soluble polymer. In some embodiments, the particulate solid composition comprises 50 to 70 weight percent of the dialkyl sulfosuccinate, and 30 to 50 weight percent of the water-soluble polymer; or 20 to 40 weight percent of the dialkyl sulfosuccinate, and 60 to 80 weight percent of the water-soluble polymer, based on the total weight of the dialkyl sulfosuccinate and the water-soluble polymer.

It is desirable that the amount of any substances other than the blend of dialkyl sulfosuccinate and a water-soluble polymer be minimized. In this way, the particulate solid composition can be used to solubilize organic substances having a water solubility of less than 1 weight percent at 25° C. without undue contamination of the organic substance. Thus, the particulate solid composition can comprise 0 to 80 weight percent each, based on the total weight of the particulate solid composition, of active pharmaceutical ingredients, generics, biosimilars, excipients, nutraceuticals, diagnostic agents, and agricultural chemicals. Within this range, the particulate solid composition can comprise 0 to 70, 60, 50, 40, 30, 20, 10, 2, 1, 0.5, or 0.1 weight percent each, based on the total weight of the particulate solid composition, of active pharmaceutical ingredients, generics, biosimilars, excipients, nutraceuticals, diagnostic agents, and agricultural chemicals. In some embodiments, the particulate solid composition comprises 0 to 40 weight percent each, based on the total weight of the particulate solid composition, of active pharmaceutical ingredients, generics, biosimilars, excipients, nutraceuticals, diagnostic agents, and agricultural chemicals. In some embodiments, the particulate solid composition is free of active pharmaceutical ingredients, generics, biologics, biosimilars, excipients, nutraceuticals, diagnostic agents, and agricultural chemicals, which means that there is no measurable amount of these materials. Agricultural chemicals include, for example, pesticides, insecticides, herbicides, biocides, and antifungals.

The particulate solid composition can comprise little or no excipient other than the sodium dioctyl sulfosuccinate, for example polysaccharides, sugar alcohols, sodium benzoate, and sodium sulfate. Thus, in some embodiments, the particulate solid composition further comprises 0 to 5 weight percent, 0 to 3 weight percent, 0 to 1 weight percent, 0 to 0.5 weight percent, or 0 to 0.1 weight percent each of polysaccharides, sugar alcohols, sodium benzoate, and sodium sulfate. In some embodiments, the particulate solid composition is free of polysaccharides, sugar alcohols, sodium benzoate, and sodium sulfate.

The particulate solid composition has many advantageous properties. For example, it is free flowing, water-soluble, and dissolves rapidly in water. Moreover, the critical micelle concentration of the dialkyl sulfosuccinate is not adversely affected. Advantageously, the free flowing particulate solid composition is easily removed from its packaging or container, with minimal particle aggregation. Thus, in some embodiments, the particulate solid composition is free flowing. Photographs of DOSS-HPMC and DOSS-copovidone blends are reproduced in FIGS. 1 (left) and 2 (left), respectively.

Advantageously, the particulate solid composition is water-soluble. Thus, in some embodiments the particulate solid composition has a distilled water solubility of 1 to 20 weight percent at 23° C., with no haze. Within this range, the particulate solid composition can have a distilled water-solubility of 1 to 10 weight percent, specifically 2 to 10 weight percent, and more specifically 5 to 10 weight percent at 23° C., with no haze. In some embodiments, the particulate solid composition has a distilled water solubility of at least 10 g/L at 23° C., with no haze. Within this range, the particulate solid composition can have a distilled water solubility of at least 30, 50, 70, 90 or 100 g/L and less than 1000, 900, 800, 700, 600, 500, 400, 300, or 200 g/L at 23° C.

Moreover, the particulate solid composition dissolves rapidly in water. Thus in some embodiments, 3 parts by weight of the particulate solid composition has a dissolution time in 87 parts by weight distilled water at 23° C. of less than 20 minutes. Within this range, the particulate solid composition can have a dissolution time in distilled water of greater than 0.1 or 1 minute and less than 15, 10, 5, 4, or 3 minutes.

Advantageously, the particulate solid composition also has a rapid dissolution rate under physiological conditions, for example at the pH of human stomach acid. For example, 3 parts by weight of the particulate solid composition can have a dissolution time in 87 parts by weight of 0.1 M hydrochloric acid at 23° C., of less than 20 minutes. 0.1 M hydrochloric acid has a pH comparable to the pH of stomach acid. Within this range, the particulate solid composition can have a dissolution time in 0.1 M hydrochloric acid of less than 15 minutes, specifically less than 10, 5, 4, or 3 minutes.

In some specific embodiments, the particulate solid composition consists essentially of 10 to 70 weight percent sodium dioctyl sulfosuccinate and 30 to 90 weight percent of a water-soluble polymer comprising poly(vinylpyrrolidone-co-vinyl acetate), hydroxypropyl cellulose, hydroxypropylmethyl cellulose, or a combination thereof, based on the total weight of the dioctyl sodium sulfosuccinate and the water-soluble polymer.

The particulate solid composition is distinguished from a physical mixture of individual dialkyl sulfosuccinate particles and water-soluble polymer particles, in that individual particles comprise both dialkyl sulfosuccinate and water-soluble polymer.

The particulate solid composition can be prepared by dissolving dialkyl sulfosuccinate and water-soluble polymer in a solvent, and removal of the solvent (drying). Solvent removal can be done by a variety of methods, including hot air drying, indirect drying, and freeze drying. Hot air, also known as convective or direct drying, involves the application of a stream of hot, dry air to the solution to be dried. An example of hot air drying is spray drying. In some embodiments, the particulate solid composition is prepared by spray drying a solution of the dialkyl sulfosuccinate and water-soluble polymer in a solvent. Thus, a method of making the particulate solid composition comprises mixing a dialkyl sulfosuccinate and a water-soluble polymer in a solvent to form a solution, and spray drying the solution to form the particulate solid composition, wherein the particulate solid composition comprises primary particles having a diameter range from 1 to 50 micrometers, and comprises, based on the total weight of the composition, 0 to 5 weight percent each of active pharmaceutical ingredients, generics, biologics, biosimilars, nutraceuticals, excipients, diagnostic agents, and agricultural chemicals.

The particulate solid composition made by spray drying comprises primary particles having a diameter range from 1 to 50 micrometers, as measured by scanning electron microscopy; and comprises, based on the total weight of the composition, 0 to less than 5 weight percent each of active pharmaceutical ingredients, generics, biologics, biosimilars, excipients, nutraceuticals, diagnostic agents, and agricultural chemicals. The particulate solid composition made by the method can further comprise aggregates of the primary particles, wherein the aggregates have a diameter range from 0.1 to 2 millimeters, as determined by optical microscopy.

The solvent can be water or an organic solvent. In some embodiments, the solvent is water, or mixtures of water and a polar organic solvent, for example a $C_{1-4}$ alcohol selected from methanol, ethanol, 2-propanol, 2-methyl-1-propanol, 2-methyl-2-propanol, 1-butanol, 2-butanol, and combinations thereof, acetone, methyl ethyl ketone, dimethyoxyethane, tetrahydrofuran, 1,4-dioxane, dimethylformamide, dimethyl sulfoxide, acetonitrile, or a combination thereof. In some embodiments, the solvent comprises 0 to 10 weight percent water and 90 to 100 weight percent of a $C_{1-4}$ alcohol, for example ethanol, based on the total weight of the solvent. Prior to spray drying, the solution solids can be 1 to 80 weight percent. Within this range the solution solids can be 1 to 70 weight percent, specifically 1 to 50 weight percent, 1 to 30 weight percent, 1 to 20 weight percent, or 1 to 10 weight percent. The solutions can be spray dried using commercially available equipment, for example a cyclone dryer. The inlet temperature depends upon the solvent boiling point and the decomposition temperatures of the dialkyl sulfosuccinate and water-soluble polymer. The inlet temperature can be 50 to 250° C., specifically 100 to 200° C. The outlet temperature can be 20 to 200° C., specifically 30 to 100° C. Advantageously, spray drying provides particulate solid compositions that are free-flowing, water-soluble, and which dissolve rapidly in water.

Indirect drying, also known as contact drying, involves heating the solution through a hot wall in contact with the solution. An example of indirect drying is drum drying. In some embodiments, the particulate solid composition is prepared by vacuum drum drying a solution of the dialkyl sulfosuccinate and water-soluble polymer in a solvent. Thus a method of making a particulate solid composition comprises: mixing a dialkyl sulfosuccinate and a water-soluble polymer in a solvent to form a solution; contacting the solution with a heated surface; and removing the solvent to form the particulate solid composition, wherein the particulate solid composition comprises, based on the total weight of the composition, 0 to less than 5 weight percent each of active pharmaceutical ingredients, generics, biologics, biosimilars, excipients, nutraceuticals, diagnostic agents, and agricultural chemicals. The solvents and solids contents can be the same as described above for spray drying. Indirect drying can be done under atmospheric pressure or under a partial vacuum, for example at a pressure of 10 to 760 mm Hg, specifically 50 to 720 mm Hg, and at a temperature of 20 to 150° C., specifically 50 to 150° C. In some embodiments, processability of the solution is improved when the solvent comprises ethanol. For example, it has surprisingly been found that a solution of sodium dioctyl sulfosuccinate and water-soluble polymer can be readily dried by vacuum drum drying when the solvent comprises ethanol, while vacuum drum drying is problematic when the solvent is water.

The particulate solid composition made by drum drying comprises flakes, and comprises, based on the total weight of the composition, 0 to less than 5 weight percent each of active pharmaceutical ingredients, generics, biologics, biosimilars, excipients, nutraceuticals, diagnostic agents, and agricultural chemicals. The flakes can have a thickness of 1 to 100 micrometers, as determined by scanning electron microscopy.

Advantageously, these methods provide particulate solid compositions that have a low volatiles content. For example, after drying, the dialkyl sulfosuccinate water-soluble polymer blend can have a solids content of 95 to 100 weight percent. Within this range, the dialkyl sulfosuccinate water-soluble polymer blend can have a solids content of 98 to 100 weight percent, specifically 99 to 100 weight percent.

Thus in some embodiments, the particulate solid composition is made by mixing a dialkyl sulfosuccinate and a water-soluble polymer in a solvent to form a solution, and spray drying the solution to form the particulate solid composition, wherein the particulate solid composition comprises primary particles having a diameter range from 1 to 50 micrometers, as measured by scanning electron microscopy, and comprises, based on the total weight of the composition, 0 to less than 5 weight percent each of active pharmaceutical ingredients, generics, biologics, biosimilars, excipients, nutraceuticals, diagnostic agents, and agricultural chemicals. All of the compositional and physical property variations of the particulate solid composition described above apply as well to the particulate solid composition produced by this method. For example, the particulate solid composition prepared by the method can further comprise aggregates of the primary particles, wherein the aggregates have a diameter range from 0.1 to 2 millimeters, as determined by optical microscopy.

The particulate solid compositions are particularly useful for improving the water solubility of organic substances having low water solubility. The organic substance, can be, for example, a natural product, a chemical compound, an oligomer, a polymer, a peptide, or a combination thereof. The organic substance can have a water solubility of 0 to less than 5 weight percent in water. Within this range, the organic compound or polymer can have a water solubility of 0 to less than 2 weight percent, 0 to less than 1 weight percent, 0 to less than 0.5 weight percent, 0 to less than 0.1 weight percent, or 0 to less than 0.01 weight percent.

Thus, a method of making a water-soluble composition comprises mixing an particulate solid composition and an organic substance having low water solubility, in amounts effective to form the water-soluble composition; wherein: the particulate solid composition comprises a blend of dialkyl sulfosuccinate and a water-soluble polymer comprising primary particles, wherein the primary particles have a diameter range from 1 to 50 micrometers, as determined by scanning electron microscopy; and 0 to less than 5 weight percent each of active pharmaceutical ingredients, generics, biologics, biosimilars, excipients, nutraceuticals, diagnostic agents, and agricultural chemicals, based on the total weight of the water-soluble composition; the particulate solid composition has a distilled water solubility of 1 to 20 weight percent at 23° C., with no haze; and the organic substance has a water solubility of less than 1 weight percent at 23° C.

The mixing can be done by methods known in the art, including blending, for example convection blending, dispersion blending, and shear blending, milling, for example wet ball milling, spray drying, gas fluidized bed drying, extrusion, for example hot melt extrusion, coating, and tableting. Spray drying and gas fluidized bed drying can be conducted on solutions of the particulate solid composition and organic substance in a solvent, for example water. In some embodiments, the mixing is done by hot melt extrusion.

Advantageously, the particulate solid composition can be used to improve the water solubility of a wide variety of organic substances, including active pharmaceutical ingredients, generics, biologics, biosimilars, excipients, nutraceuticals, diagnostic agents, or agricultural chemicals. Thus in some embodiments, the organic substance comprises an active pharmaceutical ingredient, a generic, a biologic, a biosimilar, an excipient, a nutraceutical, diagnostic agent, or an agricultural chemical. The water-soluble composition can have other advantageous properties for in vivo use, for example improved in vivo dissolution rate, resorption, and bioavailability at physiological pH values. The particulate solid composition can also be used to improve the water solubility, dispersion, or wetting of a wide variety of other useful materials, including food additives, inks, pigments, dyes, stabilizers, and oils, to name a few.

This invention includes at least the following embodiments.

Embodiment 1. A particulate solid composition comprising a blend of dialkyl sulfosuccinate and a water-soluble polymer.

Embodiment 2. The particulate solid composition of embodiment 1, wherein the water-soluble polymer is natural, semi-synthetic, synthetic, or a combination thereof.

Embodiment 3. The particulate solid composition of embodiment 1 or 2, comprising 10 to 90 weight percent of the dialkyl sulfosuccinate, and 10 to 90 weight percent of the water-soluble polymer, based on the total weight of the dialkyl sulfosuccinate and the water-soluble polymer.

Embodiment 4. The particulate solid composition of any of embodiments 1-3, consisting of the dialkyl sulfosuccinate and the water-soluble polymer.

Embodiment 5. The particulate solid composition of any of embodiments 1-3, further comprising 0 to 40 weight percent each, based on the total weight of the particulate solid composition, of active pharmaceutical ingredients, generics, biologics, biosimilars, excipients, nutraceuticals, diagnostic agents, and agricultural chemicals.

Embodiment 6. The particulate solid composition of any of embodiments 1-3, wherein the particulate solid composition is free of active pharmaceutical ingredients, generics, biologics, biosimilars, excipients, nutraceuticals, diagnostic agents, and agricultural chemicals.

Embodiment 7. The particulate solid composition of any of embodiments 1-3, further comprising 0 to 5 weight percent of polysaccharides, sugar alcohols, sodium benzoate, and sodium sulfate combined.

Embodiment 8. The particulate solid composition of any of embodiments 1-3, wherein the particulate solid composition is free of sugar alcohols, sodium benzoate, and sodium sulfate.

Embodiment 9. The particulate solid composition of any of embodiments 1-8, wherein the particulate solid composition is free flowing.

Embodiment 10. The particulate solid composition of any of embodiments 1-9, wherein the particulate solid composition has a distilled water solubility of 1 to 20 weight percent at 23° C., with no haze.

Embodiment 11. The particulate solid composition of any of embodiments 1-10, wherein 3 parts by weight of the particulate solid composition has a dissolution time in 87 parts by weight distilled water at 23° C. of less than 20 minutes.

Embodiment 12. The particulate solid composition of any of embodiments 1-11, wherein the dialkyl sulfosuccinate has the chemical structure:

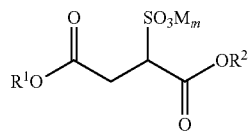

wherein $R^1$ and $R^2$ are each independently a linear or branched $C_{4-18}$ alkyl, $C_{5-18}$ cycloalkyl, $C_{7-18}$ arylalkyl, or $C_{6-18}$ aryl, unsubstituted or substituted by hydroxyl or $C_{1-18}$ alkoxy; and M is an alkali metal, an alkaline earth metal, an ammonium ion, or a combination thereof, and m is 0.5 when M is an alkaline earth metal, and m is 1 when M is an alkali metal or ammonium ion.

Embodiment 13. The particulate solid composition of embodiment 12, wherein $R^1$ and $R^2$ are both 2-ethylhexyl, M is sodium, and m is 1.

Embodiment 14. The particulate solid composition of any of embodiments 1-13, wherein the water-soluble polymer has a solubility of greater than 0.1 gram per liter when dissolved in pH 1.2 hydrochloric acid buffer for 40 minutes at 37° C.

Embodiment 15. The particulate solid composition of any of embodiments 1-13, wherein the water-soluble polymer has a solubility of greater than 0.1 gram per liter when dissolved in pH 6.8 phosphate buffer for 40 minutes at 37° C.

Embodiment 16. The particulate solid composition of any of embodiments 1-13, wherein the water-soluble polymer comprises a cellulose ether, a polysaccharide, a polyvinyl alcohol homopolymer or copolymer, a polyvinyl pyrrolidone homopolymer or copolymer, a polyvinyl caprolactam polymer or copolymer, a poly(meth)acrylate, a poly(alkylene oxide) graft copolymer, or a combination thereof.

Embodiment 17. The particulate solid composition of any of embodiments 1-13, wherein the water-soluble polymer comprises hydroxypropyl cellulose, hydroxypropylmethyl cellulose, poly(vinyl pyrrolidone-co-vinyl acetate), polyvinyl alcohol, poly(vinyl acetate-co-vinyl alcohol), poly(ethylene oxide-co-vinyl acetate-co-vinyl caprolactam), or a combination thereof.

Embodiment 18. The particulate solid composition of any of embodiments 1-3, consisting essentially of 10 to 70 weight percent sodium dioctyl sulfosuccinate and 30 to 90 weight percent of a water-soluble polymer comprising poly(vinyl pyrrolidone-co-vinyl acetate), hydroxypropyl cellulose, hydroxypropylmethyl cellulose, or a combination thereof, based on the total weight of the dioctyl sodium sulfosuccinate and the water-soluble polymer.

Embodiment 19. The particulate solid composition of any of embodiments 1-18, comprising primary particles, wherein the primary particles are spherical and have a diameter range from 1 to 50 micrometers, as determined by scanning electron microscopy.

Embodiment 20. The particulate solid composition of embodiment 19, further comprising aggregates of the primary particles, wherein the aggregates have a diameter range from 0.1 to 2 millimeters, as determined by optical microscopy.

Embodiment 21. The particulate solid composition of any of embodiments 1-18, comprising flakes.

Embodiment 22. The particulate solid composition of embodiment 21, wherein the flakes have a thickness of 1 to 100 micrometers.

Embodiment 23. The particulate solid composition of any of embodiments 1-22, wherein the particulate solid composition is amorphous.

Embodiment 24. The particulate solid composition of any of embodiments 1-22, wherein the particulate solid composition comprises a blend of crystalline dialkyl sulfosuccinate and amorphous or semi-crystalline water-soluble polymer.

Embodiment 25. A method of making a particulate solid composition, comprising: mixing a dialkyl sulfosuccinate and a water-soluble polymer in a solvent to form a solution, and spray drying the solution to form the particulate solid composition, wherein: the particulate solid composition comprises primary particles having a diameter range from 1 to 50 micrometers, as measured by scanning electron microscopy; and comprises, based on the total weight of the composition, 0 to less than 5 weight percent each of active pharmaceutical ingredients, generics, biologics, biosimilars, excipients, nutraceuticals, diagnostic agents, and agricultural chemicals.

Embodiment 26. A particulate solid composition made by the method of embodiment 25.

Embodiment 27. The particulate solid composition of embodiment 26, further comprising aggregates of the primary particles, wherein the aggregates have a diameter range from 0.1 to 2 millimeters, as determined by optical microscopy.

Embodiment 28. A method of making a particulate solid composition, comprising: mixing a dialkyl sulfosuccinate and a water-soluble polymer in a solvent to form a solution; contacting the solution with a heated surface; and removing the solvent to form the particulate solid composition, wherein the particulate solid composition comprises flakes, and comprises, based on the total weight of the composition, 0 to less than 5 weight percent each of active pharmaceutical ingredients, generics, biologics, biosimilars, excipients, nutraceuticals, diagnostic agents, and agricultural chemicals.

Embodiment 29. The method of embodiment 25 or 28, wherein the solvent comprises 0 to 10 weight percent water and 90 to 100 weight percent of a $C_{1-4}$ alcohol, based on the total weight of the solvent.

Embodiment 30. A particulate solid composition made by the method of embodiment 28 or 29.

Embodiment 31. The particulate solid composition of embodiment 30, comprising flakes having a thickness of 1 to 100 micrometers, as determined by scanning electron microscopy.

Embodiment 32. A method of making a water-soluble composition, comprising mixing a particulate solid composition and an organic substance having low water solubility, in amounts effective to form the water-soluble composition; wherein: the particulate solid composition comprises a blend of dialkyl sulfosuccinate, a water-soluble polymer, and 0 to less than 5 weight percent each of active pharmaceutical ingredients, generics, biologics, biosimilars, excipients, nutraceuticals, diagnostic agents, and agricultural chemicals, based on the total weight of the water-soluble composition; the particulate solid composition has a distilled water solubility of 1 to 20 weight percent at 23° C., with no haze; and the organic substance has a water solubility of less than 1 weight percent at 23° C.

Embodiment 33. The method of embodiment 32, wherein the organic substance comprises an active pharmaceutical ingredient, a generic, a biologic, a biosimilar, an excipient, a nutraceutical, a medical diagnostic agent, an agricultural chemical, or a combination thereof.

Embodiment 34. The particulate solid composition of any of embodiments 1-24, 26-27, and 30-31, wherein individual particles comprise both the dialkyl sulfosuccinate and the water-soluble polymer.

This invention is further illustrated by the following non-limiting examples.

EXAMPLES

The materials utilized in the examples are described below in Table 1.

TABLE 1

Materials

| Abbreviation | Description |
| --- | --- |
| DOSS | Sodium dioctyl sulfosuccinate, C.A.S. Reg. No. 577-11-7, in granular form, available from Solvay S.A., also known as sodium docusate, or docusate. |
| DOSS-70 | 70% Solution of sodium dioctyl sulfosuccinate, C.A.S. Reg. No. 577-11-7, in 23A specially denatured ethanol, available from Solvay S.A. |
| SB | Sodium benzoate, C.A.S. Reg. No. 532-32-1, available from Sigma Aldrich. |
| DOSS-SB | DOSS-SB, 85:15 by weight, C.A.S. Reg. No. 511-11-7, available as DSS Granular from Solvay S.A. |
| D-Mannitol | (2R,3R,4R,5R)-Hexan-1,2,3,4,5,6-hexol, C.A.S. Reg. No. 69-65-8, available from Harke Group. |
| SOLUPLUS ™ | Poly(ethylene glycol-vinyl acetate-N-vinyl caprolactam) graft copolymer, C.A.S. Reg. No. 02932-23-4, available from BASF. |
| HPMC | 2-Hydroxylpropylmethyl cellulose, C.A.S. Reg. No. 5004-65-3, having a viscosity of 2.4-3.6 mPa · s, available as PHARMACOAT ™ 603 from Shin-Etsu Chemical. |
| Copovidone | Poly(N-vinyl pyrrolidone-co-vinyl acetate), from 6:4 by weight N-vinylpyrollidone: vinyl acetate, C.A.S. Reg. No. 25086-89-9, available as KOLLIDON ™ VA 64, from BASF. |
| EPO | Poly(butyl methacrylate-co-(2-dimethylaminoethyl) methacrylate-co-methyl methacrylate), 1:2:1, C.A.S. Reg. No. 24938-16-7, available from Evonik Industries as EUDRAGIT ™ E PO. |
| SLS | Sodium lauryl sulfate, C.A.S. Reg. No. 151-21-3. |
| TWEEN ™ 80 | Polyoxyethylene (20) sorbitan monooleate, available from Croda. |
| TWEEN ™ 20 | Polyoxyethylene (20) sorbitan monolaurate, available from Croda. |
| Ibuprofen | (RS)-2-(4-(2-Methylpropyl)phenyl)propanoic acid, C.A.S. Reg. No. 15687-27-1. |
| Fenofibrate | Propan-2-yl 2-{4-[(4-chlorophenyl)carbonyl]phenoxy}-2-methylpropanoate, C.A.S. Reg. No. 49562-28-9. |
| Naproxen | (+)-(S)-2-(6-methoxynaphthalen-2-yl) propanoic acid, C.A.S. Reg. No. 22204-53-1. |

TABLE 1-continued

Materials

| Abbreviation | Description |
|---|---|
| Ritonavir | 1,3-Thiazol-5-ylmethyl N-[(2S,3S,5S)-3-hydroxy-5-[(2S)-3-methyl-2-{[methyl({[2-(propan-2-yl)-1,3-thiazol-4-yl]methyl})carbamoyl]amino}butanamido]-1,6-diphenylhexan-2-yl]carbamate, C.A.S. Reg. No. 155213-67-5. |
| Glipizide | N-(4-[N-(cyclohexylcarbamoyl)sulfamoyl]phenethyl)-5-methylpyrazine-2-carboxamide, C.A.S. Reg. No. 29094-61-9. |

Examples 1-5

DOSS and water-soluble polymer in the amounts provided in Table 2 were dissolved in 50 parts distilled water with gentle mixing to form solutions. The solutions were spray dried using the following conditions: Büchi B-150 Spray dryer with cyclone technology, inlet temperature of 100° C., outlet temperature of 35° C., and a flow rate of 25 g/hr.

TABLE 2

Spray Dry Solution Compositions

| Amount (parts by weight) | Example 1 | Example 2 | Example 3 | Example 4 | Example 5 |
|---|---|---|---|---|---|
| DOSS | 3.33 | 3.33 | 3.33 | 3.33 | 3.33 |
| SOLUPLUS ™ | 6.67 | 7.00 | — | — | — |
| HPMC | — | — | 6.67 | — | — |
| Copovidone | — | — | — | 3.33 | 6.67 |
| Mannitol | — | — | — | 3.33 | — |
| Distilled water | 50 | 50 | 50 | 50 | 50 |

Best results were obtained in Examples 3 and 5, in which yields of up to 75% were obtained. In Example 3, there was no precipitation of the DOSS blends in the spray-drier, and therefore no deposits or clogging of the lines.

Comparative Example 1

Comparative Example 1 is DOSS and SB in an 85:15 weight ratio, C.A.S. Reg. No. 511-11-7, available as DSS Granular from Solvay S.A.

Examples 6-8 and Comparative Example 2

In Comparative Example 2, an attempt was made to prepare DOSS-copovidone by vacuum drum drying as follows. DOSS and copovidone in a 3:1 weight ratio were dissolved in sufficient water to form a 24 wt. % solids solution. A 6" wide×8" long vacuum double drum dryer having steam heated 5/16" thick chrome plated cast iron drums and 2.00 ft² dryer surface area was used. Phenolic fiber endboard were used to contain the solution between the drums. A tempered tool steel scraper knife was located at the outer horizontal quadrant of each drum. The scraper knife makes contact with the drum surfaces to remove the dried product. The solution was fed between the drums from the top using a glass separatory funnel under a vacuum of 34 mm Hg. The solution was added under a vacuum of 34 mm Hg, and the solution temperature at the scraper knives was 132° C. However it was not possible to obtain dry DOSS-copovidone under these conditions. The product remained molten at the temperature required to evaporate the water (132° C.), and therefore could not captured by the scraper knives.

Surprisingly, it was found that DOSS-copovidone could be prepared by vacuum drum drying in the same apparatus when the components are dissolved in ethanol rather than water as follows. In Comparative Example 6, DOSS and copovidone in a 1:2 weight ratio were dissolved in denatured ethanol to form a 52.2 wt. % solids solution. The solution was fed between the drums from the top under a vacuum of 55 mm Hg. The product had assays of 32.8 wt. % DOSS and 67.3 wt. % copovidone, and a water content of 1.6 wt. %.

The process of Example 6 was readily scalable. In Example 7, 100 lbs. of DOSS-copovidone were prepared at 711 mm Hg using A 12"×18" vacuum double drum dryer having a 5/16" thick chrome plated cast iron drum and 9.4 ft² dryer surface area inside a steam-traced, stainless steel vacuum enclosure. Hot water at 60-80° C. was used for heating. The dried DOSS-copovidone formed intact sheet rolls when cut from the drum. Upon cooling, the rolls were brittle and readily milled into a powder using a cone mill. The product had DOSS and copovidone assays of 35.5 and 64.6 wt. %, respectively, and a water content of 1.6 wt. %. In Example 8, the DOSS-copovidone of Example 7 was further dried at 65° C. under vacuum for two days.

Figure 11:
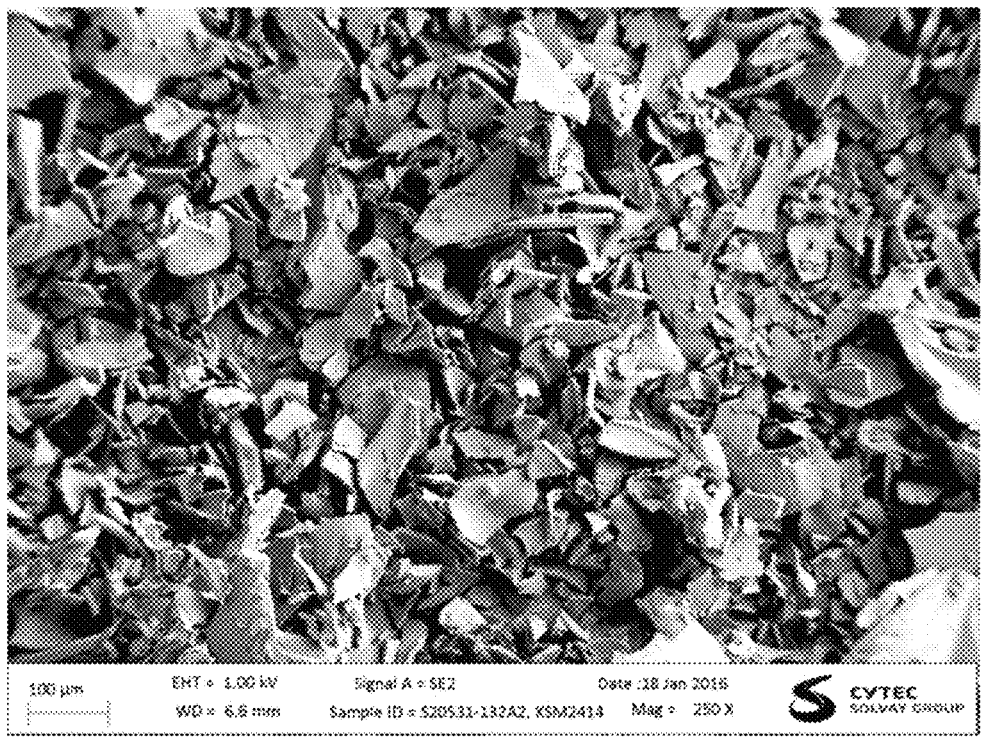
FIG. 11 is an SEM micrograph of the DOSS-copovidone of Example 8 at a magnification of 250×.
Figure 12:
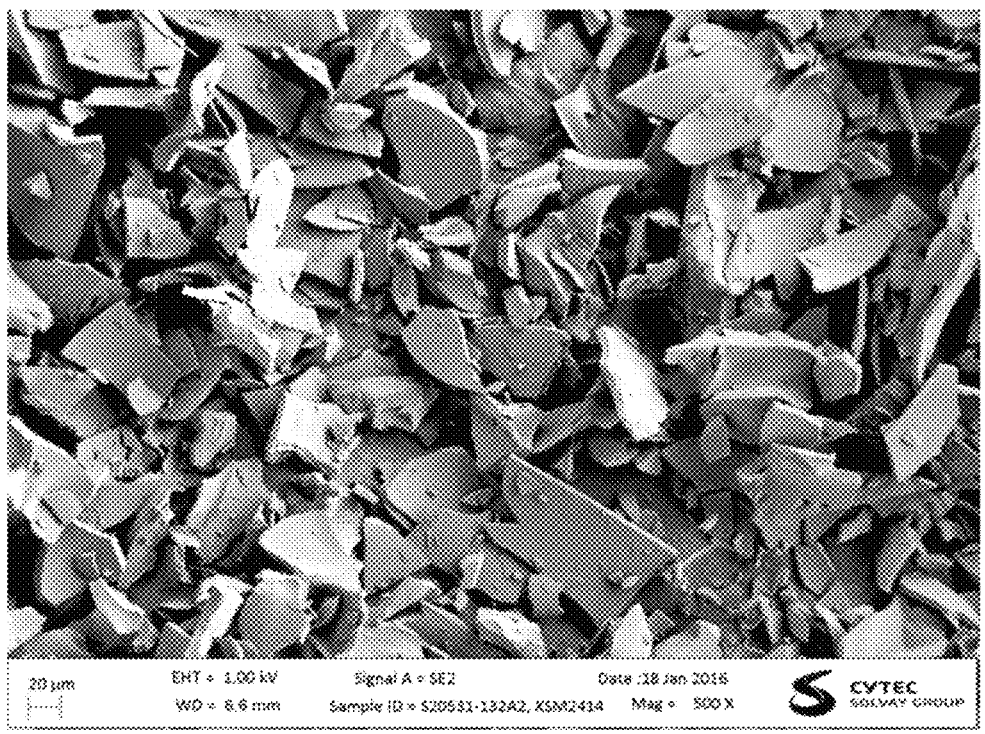
FIG. 12 is an SEM micrograph of the DOSS-copovidone of Example 8 at a magnification of 500×.
Figure 13:
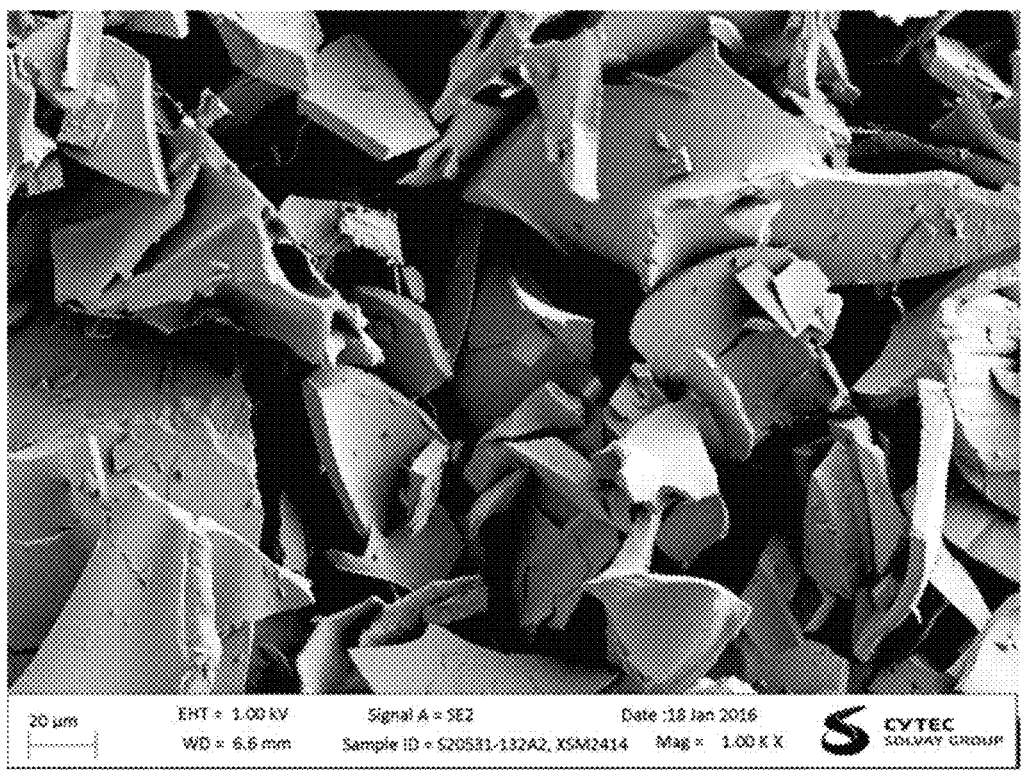
FIG. 13 is an SEM micrograph of the DOSS-copovidone of Example 8 at a magnification of 1000×.

Surprisingly, the physical form of DOSS-copovidone of Examples 7 and 8 is thin flakes. SEM photographs are provided for Example 8 in FIG. 11-13 at magnifications of 250×, 500×, and 1000×, respectively. These images are not representative of size distribution as some larger particles did not fit into field of view. Flake thickness ranges from about 1 to about 10 micrometers.

Example 9

A sample of DOSS-HPMC was prepared by spray drying as follows. PHARMACOAT™ 603 (71.2 lb., 32.3 kg) and DOSS-70 were dissolved in 581.8 lb. (263.9 kg) of USP deionized water at 100 to 110° F. (37.8 to 43.3° C.) to form an about 15 wt. % solids solution. The PHARMACOAT™ 603 was added slowly with high shear mixing. The resulting solution was spray dried at a inlet air temperature of 365 to 385° F. (185 to 196° C.), an outlet air temperature of 150 to 200° F. (65.6 to 93.3° C.). The dried product was put through a 20 Mesh HACCP Sifter Screen.

Characterization

The blends of Examples 3 and 5 and Comparative Example 1 (DSS Granular) were characterized. The results are reported in Table 3.

TABLE 3

Characterization of Dioctyl Sulfosuccinate Blends

| Components | Example 3 | Example 5 | Comp. Ex. 1 |
|---|---|---|---|
| DOSS (wt. %) | 32.8 | 32.9 | 84.5 |
| Water (wt. %) | 3.7 | 4.8 | 0.7 |

TABLE 3-continued

Characterization of Dioctyl Sulfosuccinate Blends

| Components | Example 3 | Example 5 | Comp. Ex. 1 |
|---|---|---|---|
| HPMC (wt. %) | ca. 63[a] | — | — |
| Copovidone (wt. %) | — | ca. 62[a] | — |
| SB (wt. %) | — | — | 14.8 |
| Appearance | White powder | White powder | White powder |
| Particle Size (micrometers) | 2-15 | 2-15 | >100 |
| Bulk Density at 25° C. (kg/m$^3$) | 0.27 | 0.29 | 0.37 |
| Surface Tension at CMC at 25° C. (mN/m) | 29 | 28 | 26 |
| CMC (wt. %) | 0.29 | 0.13 | 0.12 |
| BET Surface Area (m$^2$/g) | 1.6592 | 0.7180 | 2.2091 |
| Single Point Surface Area (m$^2$/g) | 1.2495 | 0.5758 | 1.1758 |
| Conc. in Water (g/L) | Solubility at 23° C., (NTU)/Appearance | | |
| 10 | 1.0, clear | 0.9, clear | 322, hazy |
| 30 | 1.6, clear | 1.8, clear | 360, hazy |
| 50 | 2.8, clear | 3.7, clear | 567, hazy |
| 100 | 266, clear | 8.3, clear | 550, hazy |

[a]Estimated from DOSS and water amounts by difference.

DOSS was assayed by titration with HYAMINE™ 1622. Water was determined by Karl Fischer titration. HMPC and copovidone contents were estimated from DOSS and water amounts by difference. Sodium benzoate was assayed by titration with tetra-n-butylammonium iodide. Photographs of DOSS (right), HPMC (center), and the DOS-HPMC blend of Example 3 (left) are reproduced in FIG. 1, and photographs of DOSS (right), copovidone (center), and the DOSS-copovidone blend of Example 5 are reproduced in FIG. 2. DOSS is in the form of sticky, waxy flakes. Advantageously, the DOSS-HPMC and DOSS-copovidone blends are free flowing, fine powders. The DOSS-HPMC and DOSS-copovidone blends have lower bulk density than both DOSS alone and DOSS-SB complex. In particular, as can be seen from Table 3, while DOSS-SB has a bulk density of 0.37 kg/m$^3$, DOSS-HMPC and DOSS-copovidone have bulk densities of 0.27 and 0.29 kg/m$^3$, respectively.

Particle size was determined by scanning electron microscopy (SEM). Images were acquired using a Zeiss Sigma VP SEM using the SE-detector at 1 KeV. FIG. 3a, FIG. 3b, and FIG. 3c depict SEM photographs of the DOSS-HPMC of Example 3 at magnifications of 500×, 3,000× and 5,000×, respectively. FIG. 4a, FIG. 4b, and FIG. 4c depict SEM photographs of the DOSS-copovidone of Example 3 at magnifications of 1,000×, 2,000× and 5,000×, respectively. FIG. 5a, FIG. 5b, and FIG. 5c depict SEM photographs of the DOSS-SB of Comparative Example 1 at magnifications of 200×, 500× and 1,000×, respectively. As can be seen from the SEM photographs, the DOSS-HPMC and DOSS-copovidone particles are spherical, while the DOSS-SB particles are irregularly-shaped. HPMC particles were macroscopic and irregularly-shaped. Advantageously, DOSS-HPMC and DOSS-copovidone have volume particle diameter ranges of 2 to 15 micrometers, while the DOSS-SB blend has a volume particle diameter range of about 100 micrometers and above, as determined by SEM.

Surface Area

Surface area is a measure of the exposed surface of a solid sample on a molecular scale. BET surface area was measured according to the Brunauer, Emmet and Teller model. Test samples were prepared by simultaneous heating and evacuating or flowing gas over the sample to remove vaporized impurities. The prepared samples were then cooled with liquid nitrogen and analyzed by measuring the volume of krypton gas absorbed at specific pressures.

Surface Tension

The surface tensions of solutions of Examples 3 (DOSS-HPMC) and 5 (DOSS-copovidone, and Comparative Example 1 (DOSS) were measured at different concentrations in distilled water. The results are plotted in FIG. 6. Critical micelle concentration (CMC) and surface tension at the CMC are provided in Table 3. As can be seen from Table 3, the CMC, and the surface tension at CMC, for the DOSS-HPMC and DOSS-copovidone blends are comparable to the CMC and surface tension at CMC for DOSS. Thus, the water-soluble polymers are expected to have little or no impact on the surface activity of DOSS, and its efficacy as a surfactant.

Water Solubility

DOSS, USP grade, is available as solid white waxy rolls. It has a solubility in water of only about 1 in 70 parts per R. C. Rowe, P. J, Sheskey, M. E. Quinn (Ed.), *Handbook of Pharmaceutical Excipients*, 6th ed. pp. 244-246. This corresponds to a solubility of 15 g/L. DOSS-SB, available as DSS Granular, has comparable water solubility. Surprisingly DSS provided as DOSS-copovidone and DOSS-HPMC provide stable supersaturated solutions of DOSS. Water solubility is defined herein as a concentration of dioctyl sulfosuccinate blend that provides a clear solution in water, i.e. has a turbidity of less than 200 Nephelometric Turbidity Units (NTU's). Turbidity was measured using a nephelometer with the detector set up to the side of the light beam. As can be seen from Table 3, DOS S-HPMC provides clear solutions up to at least 50 g/L DOSS, the actual water solubility being between 50 to 100 g/L. DOSS-copovidone provides clear solutions up to at least 100 g/L, indicated a water solubility exceeding 100 g/L. In contrast, the DOSS-SB blend is insoluble, even at 10 g/L, providing a hazy solution having a turbidity of 322 NTU's. These data show that surprisingly, DOSS-HPMC and DOSS-copovidone provide stable supersaturated solutions of DOSS in water.

Powder X-Ray Diffraction (PXRD)

Approximately 1 gram of the sample was placed on a standard aluminum holder and was used for X-ray diffraction (XRD) on a Rigaku Multiflex X-ray diffractometer using a Cu Kα radiation source (λ=0.1541 nm) at 40 kV and 20 mA. The data was collected between the scan range of 5-60° 2θ and a step size of 0.02°. The diffractograms were analyzed by Jade software version 9.0, with reference patterns from the Powder Diffraction File 4 (PDF-4) database licensed by the International Center for Diffraction Data (ICDD).

Figure 7:
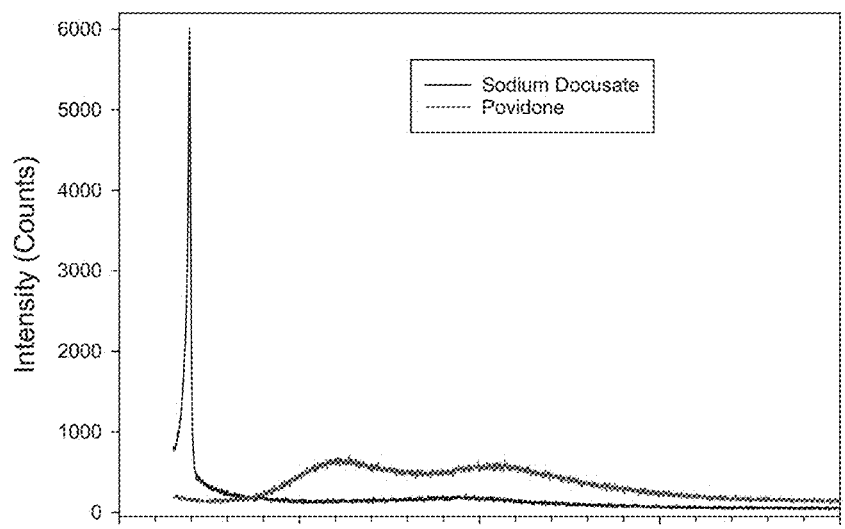
FIG. 7 depicts individual powder X-ray diffraction patterns for DOSS and copovidone, overlaid.
Figure 8:
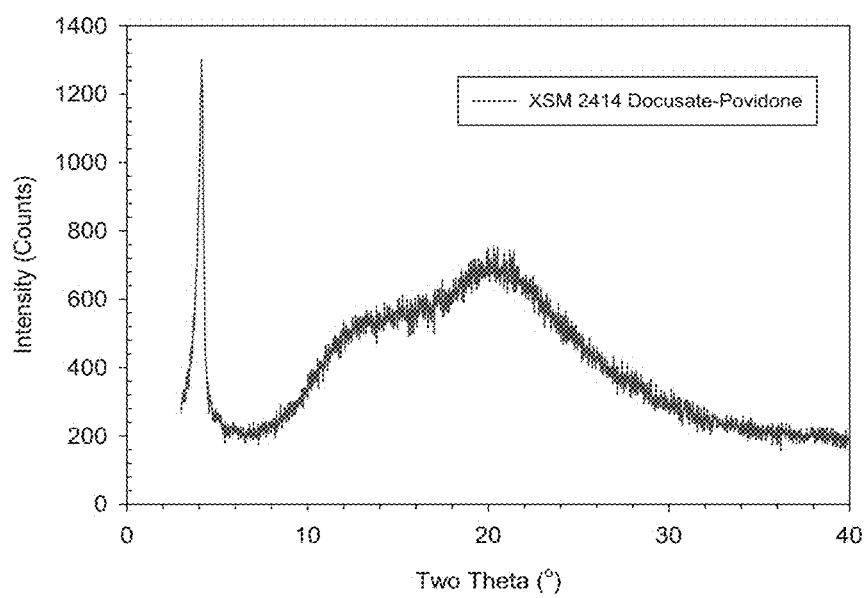
FIG. 8 depicts the powder X-ray diffraction pattern for DOSS-copovidone prepared by vacuum drum drying.

FIG. 7 depicts individual powder X-ray diffraction (PXRD) patterns for DOSS and copovidone, overlaid. (Sodium docusate is another name for DOSS.) The sharp peak at a scattering angle (2 theta) of about 4° for DOSS is indicative of a crystalline morphology. The broad peaks for copovidone are indicative of an amorphous or semi-crystalline morphology. FIG. 8 depicts the PXRD pattern for DOSS-copovidone (Docusate is another name for DOSS, and XSM-2414 is a code for DOSS-copovidone). The sharp peak at a scattering angle of about 4° and the broad peak at a scattering angle of about 21° indicate the presence of both crystalline DOSS and amorphous or semi-crystalline copovidone in the DOSS-copovidone blend.

Figure 9:
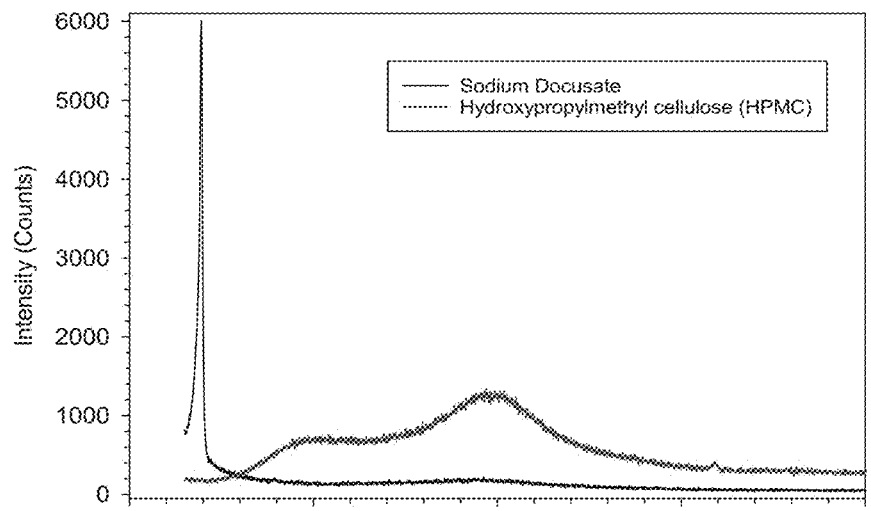
FIG. 9 depicts individual powder X-ray diffraction patterns for DOSS and HPMC, overlaid.
Figure 10:
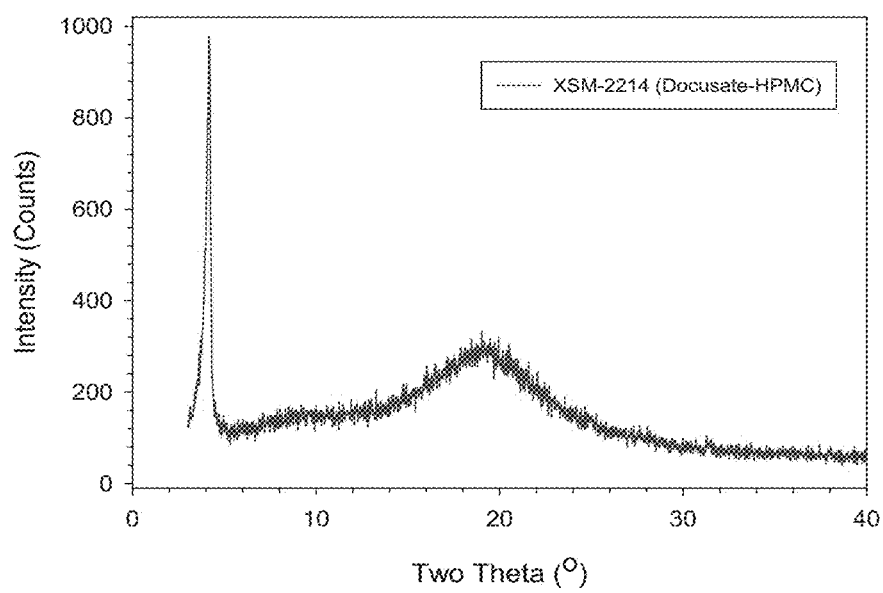
FIG. 10 depicts the powder X-ray diffraction pattern for DOSS-HPMC prepared by spray drying.

FIG. 9 depicts individual PXRD patterns for DOSS and HPMC, overlaid. (Sodium docusate is another name for DOSS.) The broad peaks for HPMC are indicative of an amorphous or semi-crystalline morphology. FIG. 10 depicts the powder X-ray diffraction pattern for DOSS-HPMC prepared by vacuum drum drying. (Docusate is another name for DOSS, and XSM-2214 is a code for DOSS-HPMC) As with the PXRD pattern for DOSS-copovidone, the sharp peak at a scattering angle of about 4° and the broad peak at a scattering angle of about 19° indicate the presence of both crystalline DOSS and amorphous or semi-crystalline HPMC in the DOSS-HPMC blend.

Contact Angle

A factor which contributes to the bioavailability of active pharmaceutical ingredients (API's) is the wetting of the API by an aqueous solution at a physiological pH. Wetting can affect dissolution rates of the API in the aqueous solution. Wetting can be assessed by measuring the contact angle between an aqueous solution and an API. In these examples, the sessile drop method was used to determine contact angles. Pellets of API were produced using an X-press 3630 with a 35-mm pressing die. The API was pressed into a 35-mm diameter aluminum pan using the standard 30-ton cycle in order to produce a flat surface. Drops (10-μL) of a 0.1% test solution of an excipient were used. The test solution was 0.1 M HCl, to simulate physiological conditions in the human stomach. As can be seen from Table 4, contact angles of less than 5° were obtained for ibuprofen, fenofibrate, naproxen and glipizide when the excipient was DOSS, regardless of the physical form of DOSS used, be it DOSS, DOSS-SB, DOSS-HPMC, or DOSS-copovidone. These data show that the presence of HPMC or copovidone does not adversely affect the advantageous effect DOSS has on contact angles with the API's.

TABLE 4

Contact Angle of Excipient Solutions in 0.1M HCl with API's

| Excipient | Contact Angle (°) | | | | |
|---|---|---|---|---|---|
| | Ibuprofen | Fenofibrate | Naproxen | Ritonavir | Glipizide |
| DOSS-HPMC | <5 | <5 | <5 | 23 | <5 |
| DOSS-copovidone | <5 | <5 | <5 | 25 | <5 |
| DOSS | <5 | <5 | <5 | 20 | <5 |
| DOSS-SB | <5 | <5 | <5 | 33 | <5 |
| SLS | 54 | 47 | 34 | 57 | 43 |
| TWEEN ™ 20 | 45 | 58 | 48 | 40 | 42 |
| TWEEN ™ 80 | 68 | 70 | 52 | 51 | 55 |

Dissolution Time

Dissolution times for DOSS, DOSS-SB, HPMC, copovidone, DOSS-HPMC, and DOSS-copovidone were measured as follows. The excipient (3 parts by weight) was added to 87 parts by weight of deionized water at 23° C. with mechanical stirring. Stirring was interrupted approximately every minute for less than 10 seconds to make a visual observation. The results are summarized in Table 5. Dissolution of DOSS, which is supplied in granular form, in water was difficult, taking about 40 minutes to dissolve. Dissolution time was improved by the addition of sodium benzoate to the DOSS, but was still about 20 minutes for the DOSS-SB. Advantageously, the present particulate solid compositions, DOSS-HPMC and DOSS-copovidone, dissolve in water faster than DOSS alone, and also faster than DOSS-SB blends. As can be seen from Table 6, while DOSS, dissolved in 37 minutes, the DOSS-HPMC of Example 3 dissolved in only 10 minutes. Moreover, while DOSS dissolved in 41:20 in a separate experiment, the DOSS-copovidone of Example 5 dissolved in only 3:30.

TABLE 5

Dissolution Times in Deionized Water

| Material | Dissolution Time (min.) |
|---|---|
| DOSS | 37 |
| HPMC | 16 |
| DOSS Time + HPMC Time | 53 |
| DOSS-HPMC (Ex. 3) | 10 |
| DOSS | 41 |
| Copovidone | 4 |
| DOSS-copovidone (Ex. 5) | 3-4 |
| DOSS-SB | 20 |

Further water dissolution studies were carried out on the DOSS-copovidone of Examples 7 and 8, and the DOSS-HPMC of Example 9. This time, 2.000±0.0200 g excipient was dissolved in 200 g of deionized water, or 200 g of 0.1 M HCl. Dissolution rates in both deionized water and 0.1 M hydrochloric acid (to model human stomach conditions) were evaluated. The results are summarized below in Table 6. As can be seen from the table, dissolution times in 0.1 M HCl were comparable to dissolution times in deionized water, although DOSS-HPMC was somewhat slower to dissolve in 0.1 M HCl.

TABLE 6

Dissolution Times in Deionized Water and 0.1M HCl

| | Dissolution Time (min) | | |
|---|---|---|---|
| Example | 7 | 8 | 9 |
| Type | DOSS-copovidone | DOSS-copovidone | DOSS-HPMC |
| Deionized water | 3 | 4 | 7 |
| 0.1M HCl | 3.5 | 4 | 10 |

Fourier Transform Infrared Imaging of DOSS-HPMC

Fourier Transform infrared (FTIR) measurements and imaging were made on an Agilent Technologies Cary 600 Series FTIR imaging system at a resolution of 4 cm$^{-1}$ by averaging 64 scans and using Resolutions Pro software (version 5.2.0, Agilent). All three available modes of measurement were employed—reflection mode, attenuated total reflection (ATR) mode, and transmission mode (transmitted reflection, or transflection). In reflection mode chemical composition information was obtained from the sample surface by analyzing diffusely scattered and specularly reflected IR radiation. In ATR mode, chemical composition information was obtained from the sample surface by analyzing evanescent wave phenomena. In transmission mode, chemical composition information was obtained from the bulk of the sample. For reflection and transmitted reflection modes, a gold coated mirror was used as a reference. Also for the transmitted reflection mode, the samples were compressed in a diamond compression cell. In some of the FTIR imaging, particles on the high end of the particle size distribution were utilized, due to limitations in resolution of the methods.

Figure 14:
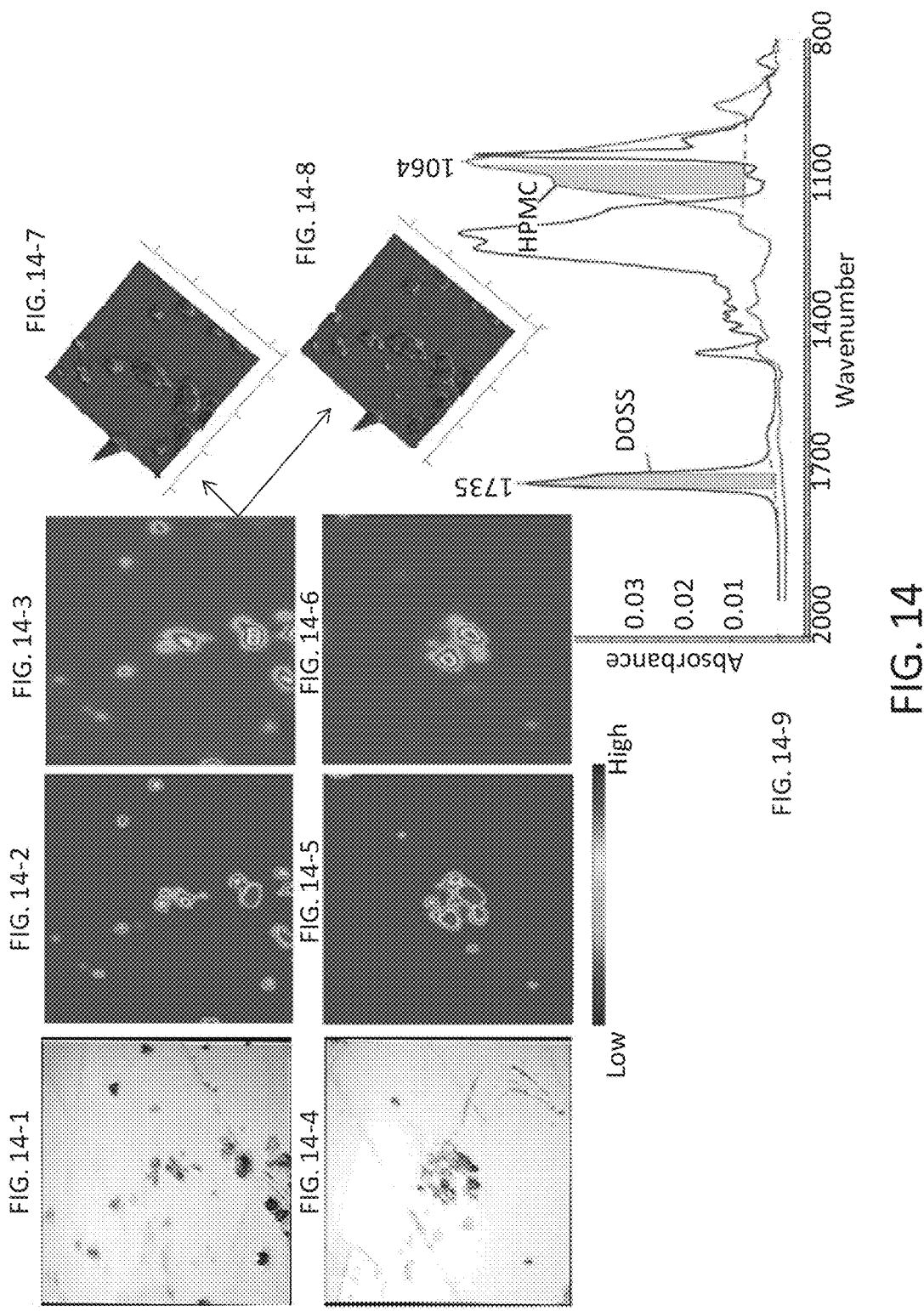
FIG. 14 depicts visible micrographs and FTIR vibrational images, measured in reflectance mode, of two samples of DOSS-HPMC particles with a 350×350 micrometer field of view.

Samples (1) and (2) of DOSS-HPMC showing individual particles and particle aggregates were placed on a gold-coated mirror, and analyzed by visible micrography and FTIR. The results are depicted in FIG. 14. The results for Sample (1) are presented in FIGS. 14-1 to 14-3; and the results for Sample (2) are presented in FIGS. 14-4 to 14-6.

Figure 2:
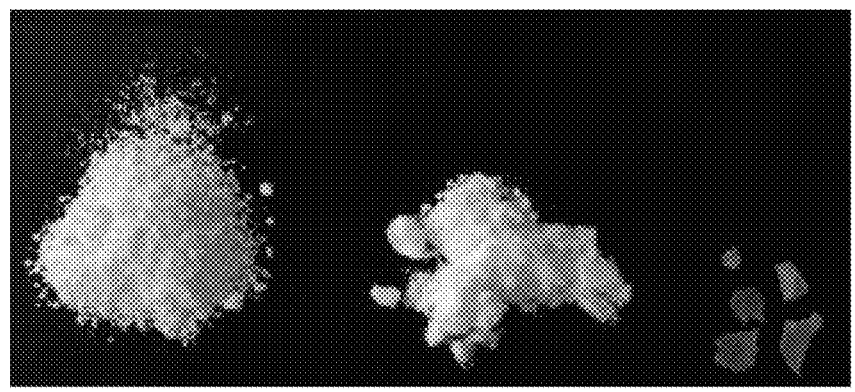
FIG. 2 depicts photographs of DOSS (right), copovidone (center), and the DOSS-copovidone of Example 5 (left).
Figure 6:
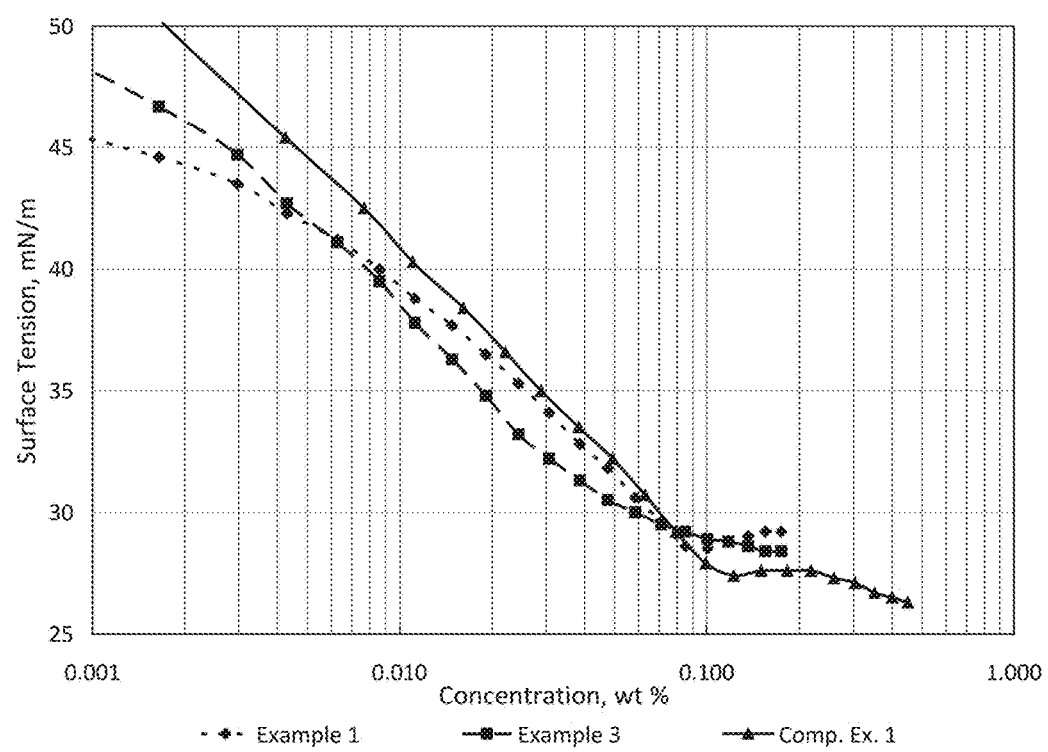
FIG. 6 is a plot of surface tension in millinewtons per meter (mN/m) as a function of concentration in weight percent (wt. %), for DOSS-HPMC (Example 3), DOSS-copovidone (Example 5), and DOSS-SB (Comparative Example 1).

Visible micrographs of Samples (1) and (2) are in FIGS. 14-1 and 14-4, respectively. Two-dimensional FTIR vibrational images of Samples (1) and (2), measured in reflectance mode, are in FIGS. 14-2 and 14-3, and in FIGS. 14-5 and 14-6, respectively. The field of view for both samples was 350×350 µm. The exact spatial resolution was dependent on the analytical wavelength used to generate the images. However it was generally approximately 5 µm. Analytical wavelengths of 1735 cm$^{-1}$ for DOSS and 1064 cm$^{-1}$ for HPMC were selected based on the overlaid one-dimensional FTIR spectra of DOSS and HPMC in FIG. 14-9. FIGS. 14-2 and 14-5 are DOSS-specific images, based on absorption at 1735 cm$^{-1}$, and FIGS. 14-3 and 14-6 are HPMC-specific images, based on absorption at 1064 cm$^{-1}$. The data for Sample (1) were further converted into the three-dimensional DOSS- and HPMC-specific images of FIGS. 14-7 and 14-8, respectively. As can be seen from comparing the visible micrographs and the FTIR vibrational images, at a resolution of approximately 5 µm, each particle contains both DOSS and HPMC. Thus, the DOSS-HPMC is not merely a physical mixture of individual DOSS and HPMC particles. Instead, it is an intimate blend of DOSS and HPMC.

Figure 15:
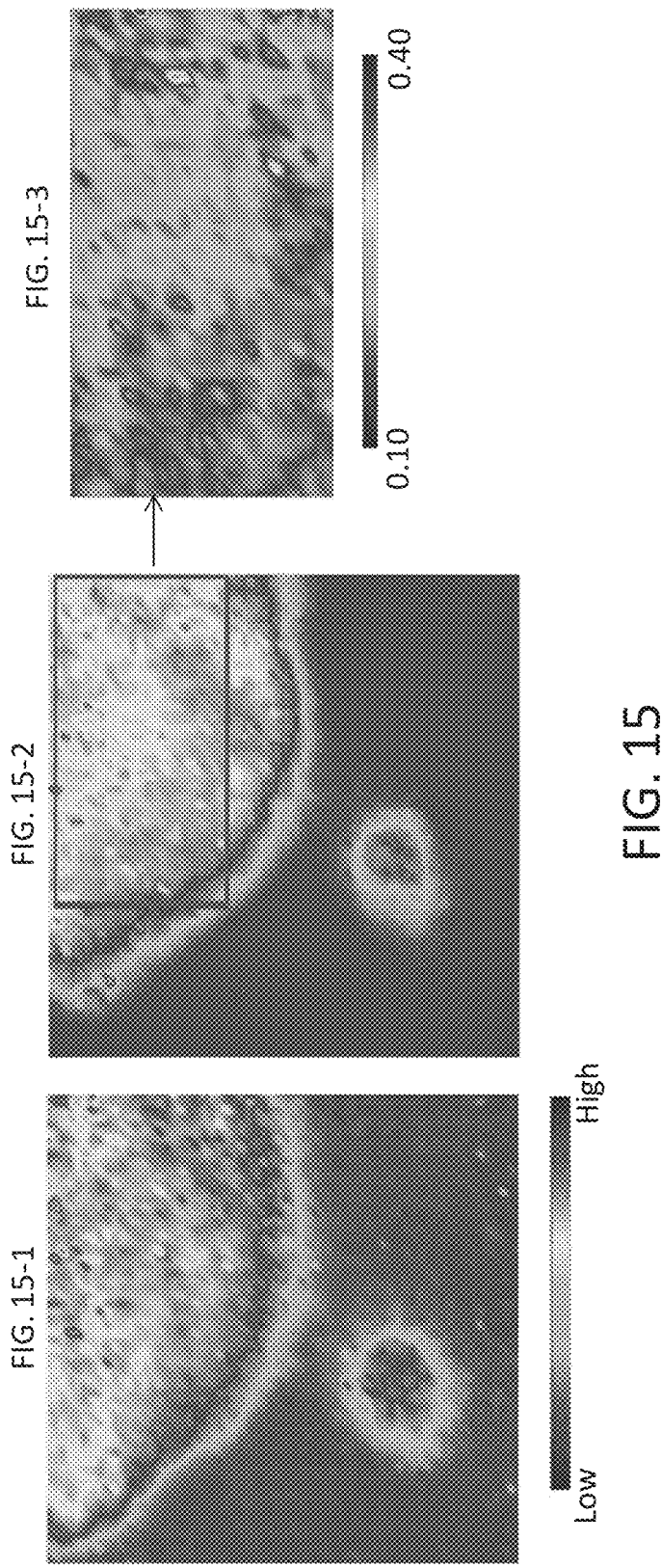
FIG. 15 depicts FTIR attenuated total reflectance (ATR) images of a sample of DOSS-HPMC with a 70×70 micrometer field of view, including a DOSS-specific image (FIG. 15-1), an HPMC-specific image (FIG. 15-2), and a 25×47 micrometer HPMC-normalized DOSS distribution image (FIG. 15-3).

A sample of DOSS-HPMC particles of different sizes was analyzed by FTIR attenuated total reflectance (ATR) imaging. ATR was utilized, because it provides an approximately 4-fold improvement in spatial resolution as compared to reflection or transmission imaging. The results are depicted in FIG. 15. The field of view was 70×70 µm. The imaging was conducted to a depth of approximately 1 µm from the particle surface, and at a spatial resolution of approximately 1 µm. FIG. 15-1 is a DOSS-specific image and FIG. 15-2 is an HPMC-specific image. A 25×47 µm portion of the HPMC-specific image was normalized for HPMC content, and the DOSS content at normalized HPMC content is depicted in FIG. 15-3. The normalized FTIR image on the right was generated by normalizing the absorbance at 1064 cm$^{-1}$, the analytical wavelength for HPMC, to 1.0 for every pixel, and displaying the resulting normalized absorbance at 1735 cm$^{-1}$, which is the analytical wavelength for DOSS. As can be seen from FIG. 15-3, the ratio of DOSS to HPMC is not constant, which indicates that there are domains of varying ratios of DOSS and HPMC for the surface layer to a depth of approximately 1 µm and at a spatial resolution of approximately 1 µm.

Figure 16:
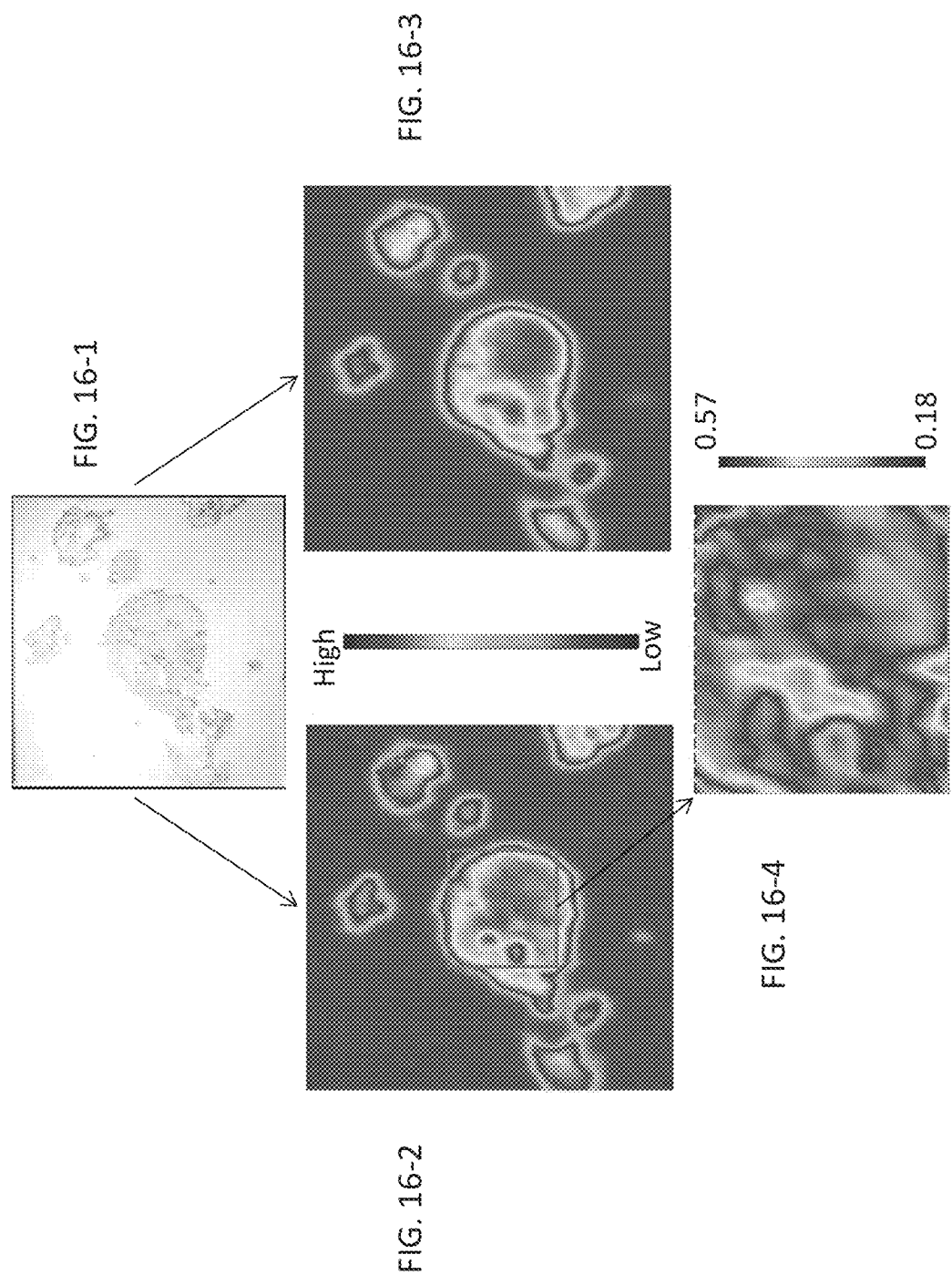
FIG. 16 depicts a visible micrograph (FIG. 16-1) and FTIR vibrational images, measured in transmission mode, of a sample of DOSS-HPMC with a 350×350 micrometer field of view, including a DOSS-specific image (FIG. 16-2), an HPMC-specific image (FIG. 16-3), and an HMPC-normalized DOSS distribution image with a 110×110 micrometer field of view (FIG. 16-4).

A sample of DOSS-HPMC showing individual particles and particle aggregates was flattened in a diamond compression cell and analyzed by visible micrography and FTIR imaging. The results are depicted in FIG. 16. The field of view was 350×350 µm. The exact spatial resolution was dependent on the analytical wavelength used to generate the images. However it was generally approximately 5 µm. A visible micrograph is in FIG. 16-1, and FTIR vibrational images, measured in transmission mode, are in FIGS. 16-2 and 16-3. Analytical wavelengths of 1735 cm$^{-1}$ for DOSS and 1064 cm$^{-1}$ for HPMC were selected based on the overlaid FTIR spectra of DOSS and HPMC in FIG. 14-9. FIG. 16-2 is a DOSS-specific image, based on absorption at 1735 cm$^{-1}$, and FIG. 16-3 is an HPMC-specific image, based on absorption at 1064 cm$^{-1}$. A 110×110 µm portion of the HPMC-specific image was normalized for HPMC content, and the DOSS absorbance at normalized HPMC absorbance is depicted in FIG. 16-4. The normalized IR image was generated by normalizing the absorbance at 1064 cm$^{-1}$, the analytical wavelength for HPMC, to 1.0 for every pixel, and displaying the resulting normalized absorbance at 1735 cm$^{-1}$, which is the analytical wavelength for DOSS. As can be seen from FIG. 16-4, the ratio of DOSS to HPMC is again not constant, which again indicates that there are domains of varying ratios of DOSS and HPMC throughout the bulk of the sample.

Fourier Transform Infrared Imaging of DOSS-Copovidone

A sample of DOSS-copovidone particle aggregates was flattened in a diamond compression cell and analyzed by visible micrography and FTIR imaging. The results are depicted in FIG. 17. The field of view was 350×350 µm. The exact spatial resolution was dependent on the analytical wavelength used to generate the images. However it was generally approximately 5 µm. A visible micrograph is in FIG. 17-5, and FTIR vibrational images, measured in transmission mode, are in FIGS. 17-1 and 17-2. Analytical wavelengths of 2958 and 2874 cm$^{-1}$ for DOSS (FIGS. 17-1 and 17-2, respectively) and 1494 cm$^{-1}$ for copovidone (FIG. 17-3) were selected based on the overlaid IR spectra of DOSS and copovidone in FIG. 17-4. FIGS. 17-1 and 17-2 are DOSS-specific images, based on the absorptions at of 2958 and 2874 cm$^{-1}$, respectively, and FIG. 17-3 is a copovidone-specific image, based on the absorption at 1494 cm$^{-1}$. FIG. 17-6 is a three-dimensional representation of the two-dimensional copovidone image of FIG. 17-3. As can be seen from the FTIR images, at a resolution of approximately 5 µm, each pixel of the sample contains both DOSS and copovidone. Thus the DOSS-copovidone is not merely a physical mixture of individual DOSS and copovidone particles. Instead, it is an intimate blend of DOSS and copovidone through the bulk of the sample.

A sample of DOSS-copovidone was compressed into a flat pellet using a diamond compression cell, and analyzed by visible micrography and FTIR imaging. The results are depicted in FIG. 18. A visible micrograph is in FIG. 18-1, and FTIR vibrational images, measured in transmission mode, are in FIGS. 18-2 and 18-4. The exact spatial resolution was dependent on the analytical wavelength used to generate the images. However it was generally approximately 5 µm. FIG. 18-2 is a DOSS-specific image, based on the absorption at 2874 cm$^{-1}$, and FIG. 18-4 is a copovidone-specific image, based on the absorption at 1494 cm$^{-1}$. FIG. 18-3 is a three-dimensional representation of the two-dimensional DOSS image of FIG. 18-2, and FIG. 18-5 is a three-dimensional representation of the two-dimensional copovidone image of FIG. 18-4. As can be seen from the FTIR images, at a resolution of approximately 5 µm, each pixel of the sample contains both DOSS and copovidone. This is further evidence that DOSS-copovidone is not merely a physical mixture of individual DOSS and copovidone particles. Instead, it is an intimate blend of DOSS and copovidone.

As used herein, "polymers" refers to homopolymers and copolymers, unless specified otherwise.

When a composition is described as "free of" a given material, this indicates that there is no measurable amount of the material in the composition.

Unless specified otherwise, solubility is expressed in units of weight percent, and the units of weight percent are based on the total weight of the solute and solvent.

As used herein, the construction, "DOSS-water soluble polymer", for example "DOSS-HPMC" and "DOSS-copovidone", refers to the particulate solid composition made by methods disclosed herein, wherein individual particles of the particulate solid contains both DOSS and the water-soluble polymer. Thus, it refers to an intimate mixture of DOSS and water-soluble polymer, rather than a physical mixture of DOSS particles and water-soluble polymer particles. Thus, "DOSS-water soluble polymer" can also be referred to as a DOSS-water soluble blend, for example a DOSS-HPMC blend or DOSS-copovidone blend.

As used herein, the terms "a" and "an" do not denote a limitation of quantity, but rather the presence of at least one of the referenced items. Recitation of ranges of values are merely intended to serve as a shorthand method of referring individually to each separate value falling within the range, and each separate value is incorporated into this specification as if it were individually recited. Thus each range disclosed herein constitutes a disclosure of any sub-range falling within the disclosed range. Disclosure of a narrower range or more specific group in addition to a broader range or larger group is not a disclaimer of the broader range or larger group. All ranges disclosed herein are inclusive of the endpoints, and the endpoints are independently combinable with each other. "Comprises" as used herein includes embodiments "consisting essentially of" or "consisting of" the listed elements.

While typical embodiments have been set forth for the purpose of illustration, the foregoing descriptions should not be deemed to be a limitation on the scope herein. Accordingly, various modifications, adaptations, and alternatives can occur to one skilled in the art without departing from the spirit and scope herein.

What is claimed is:

1. A particulate solid composition comprising a blend of 10 to 90 weight percent of a dialkyl sulfosuccinate and 10 to 90 weight percent of a water-soluble polymer, based on the total weight of the particulate solid composition.

2. The particulate solid composition of claim 1, wherein the water-soluble polymer is natural, semi-synthetic, synthetic, or a combination thereof.

3. The particulate solid composition of claim 1, consisting of the dialkyl sulfosuccinate and the water-soluble polymer.

4. The particulate solid composition of claim 1, further comprising 0 to 40 weight percent each, based on the total weight of the particulate solid composition, of active pharmaceutical ingredients, generics, biologics, biosimilars, excipients, nutraceuticals, diagnostic agents, and agricultural chemicals.

5. The particulate solid composition of claim 1, wherein the particulate solid composition is free of active pharmaceutical ingredients, generics, biologics, biosimilars, excipients, nutraceuticals, diagnostic agents, and agricultural chemicals.

6. The particulate solid composition of claim 1, further comprising 0 to 5 weight percent of polysaccharides, sugar alcohols, sodium benzoate, and sodium sulfate combined.

7. The particulate solid composition of claim 1, wherein the particulate solid composition is free of sugar alcohols, sodium benzoate, and sodium sulfate.

8. The particulate solid composition of claim 1, wherein the particulate solid composition is free flowing.

9. The particulate solid composition of claim 1, wherein the particulate solid composition has a distilled water solubility of 1 to 20 weight percent at 23° C., with no haze.

10. The particulate solid composition of claim 1, wherein 3 parts by weight of the particulate solid composition has a dissolution time in 87 parts by weight distilled water at 23° C. of less than 20 minutes.

11. The particulate solid composition of claim 1, wherein the dialkyl sulfosuccinate has the chemical structure:

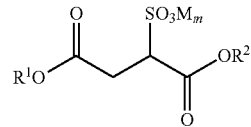

wherein $R^1$ and $R^2$ are each independently a linear or branched $C_{4-18}$ alkyl, $C_{5-18}$ cycloalkyl, $C_{7-18}$ arylalkyl, or $C_{6-18}$ aryl, unsubstituted or substituted by hydroxyl or $C_{1-18}$ alkoxy; and M is an alkali metal, an alkaline earth metal, an ammonium ion, or a combination thereof, and m is 0.5 when M is an alkaline earth metal, and m is 1 when M is an alkali metal or ammonium ion.

12. The particulate solid composition of claim 11, wherein $R^1$ and $R^2$ are both 2-ethylhexyl, M is sodium, and m is 1.

13. The particulate solid composition of claim 1, wherein the water-soluble polymer has a solubility of greater than or equal to 0.1 gram per liter when dissolved in pH 1.2 hydrochloric acid buffer for 40 minutes at 37° C.

14. The particulate solid composition of claim 1, wherein the water-soluble polymer has a solubility of greater than 0.1 gram per liter when dissolved in pH 6.8 phosphate buffer for 40 minutes at 37° C.

15. The particulate solid composition of claim 1, wherein the water-soluble polymer comprises a cellulose ether, a polysaccharide, a polyvinyl alcohol homopolymer or copolymer, a polyvinyl pyrrolidone homopolymer or copolymer, a polyvinyl caprolactam polymer or copolymer, a poly(meth)acrylate, a poly(alkylene oxide) graft copolymer, or a combination thereof.

16. The particulate solid composition of claim 1, wherein the water-soluble polymer comprises hydroxypropyl cellulose, hydroxypropylmethyl cellulose, poly(vinyl pyrrolidone), poly(vinyl pyrrolidone-co-vinyl acetate), polyvinyl alcohol, poly(vinyl acetate-co-vinyl alcohol), poly(ethylene oxide-co-vinyl acetate-co-vinyl caprolactam), or a combination thereof.

17. The particulate solid composition of claim 1, consisting essentially of 10 to 70 weight percent sodium dioctyl sulfosuccinate and 30 to 90 weight percent of a water-soluble polymer comprising poly(vinylpyrrolidone-co-vinyl acetate), hydroxypropyl cellulose, hydroxypropylmethyl cellulose, or a combination thereof, based on the total weight of the dioctyl sodium sulfosuccinate and the water-soluble polymer.

18. The particulate solid composition of claim 1, comprising primary particles, wherein the primary particles are spherical and have a diameter range from 1 to 50 micrometers, as determined by scanning electron microscopy.

19. The particulate solid composition of claim 18, further comprising aggregates of the primary particles, wherein the aggregates have a diameter range from 0.1 to 2 millimeters, as determined by optical microscopy.

20. The particulate solid composition of claim 1, comprising flakes.

21. The particulate solid composition of claim 20, wherein the flakes have a thickness of 1 to 100 micrometers.

22. The particulate solid composition of claim 1, wherein the particulate solid composition is amorphous.

23. The particulate solid composition of claim 1, wherein the particulate solid composition comprises a blend of crystalline dialkyl sulfosuccinate and amorphous or semi-crystalline water-soluble polymer.

24. A method of making a particulate solid composition as defined by claim 1, the method comprising:

mixing 10 to 90 weight percent of a dialkyl sulfosuccinate and 10 to 90 weight percent of a water-soluble polymer, based on the total weight of the dialkyl sulfosuccinate and the water-soluble polymer, in a solvent to form a solution, and spray drying the solution to form the particulate solid composition, wherein the particulate solid composition is further characterized by having primary particles having a diameter range from 1 to 50 micrometers, as measured by scanning electron microscopy; and wherein the particulate solid composition further comprises, based on the total weight of the particulate solid composition, 0 to 3 weight percent of sodium benzoate and 0 to less than 5 weight percent each of one or more compositions chosen from active pharmaceutical ingredients, generics, biologics, biosimilars, excipients, nutraceuticals, diagnostic agents, or agricultural chemicals.

25. A particulate solid composition made by the method of claim 24.

26. The particulate solid composition of claim 25, further comprising aggregates of the primary particles, wherein the aggregates have a diameter range from 0.1 to 2 millimeters, as determined by optical microscopy.

27. The particulate solid composition of claim 1, wherein individual particles comprise both the dialkyl sulfosuccinate and the water-soluble polymer.

28. A particulate solid composition according to claim 11 further comprising 0 to 40 weight percent of excipients, and 0 to 0.1 weight percent of one or more composition chosen from active pharmaceutical ingredients, generics, biologics, biosimilars, nutraceuticals, diagnostic agents, or agricultural chemicals, wherein all weight percents are based on the total weight of the particulate solid composition.

29. A particulate solid composition according to claim 28, wherein the water-soluble polymer comprises hydroxypropyl cellulose, hydroxypropylmethyl cellulose, poly(vinyl pyrrolidone), poly(vinyl pyrrolidone-co-vinyl acetate), polyvinyl alcohol, poly(vinyl acetate-co-vinyl alcohol), poly(ethylene oxide-co-vinyl acetate-co-vinyl caprolactam), or a combination thereof.

30. A particulate solid composition according to claim 29 comprising primary particles or flakes, wherein the primary particles are spherical and have a diameter from 1 micrometer to 50 micrometers, and wherein the flakes have a thickness from 1 micrometer to 100 micrometers, as determined by scanning electron microscopy.

31. A particulate solid composition according to claim 30, wherein the particulate solid composition comprises aggregates of the primary particles, wherein the aggregates have a dimeter from 0.1 millimeter to 2 millimeters, as determined by optical microscopy.

32. A particulate solid composition according to claim 30, wherein the particulate solid composition is amorphous.

33. A particulate solid composition according to claim 30, wherein the particulate solid composition comprises a blend of crystalline dialkyl sulfosuccinate and amorphous or semi-crystalline water-soluble polymer.

34. A particulate solid composition according to claim 30, wherein the particulate solid is free flowing.

* * * * *